United States Patent
Fujii et al.

(10) Patent No.: US 10,865,372 B2
(45) Date of Patent: Dec. 15, 2020

(54) NEURON CULTIVATION DEVICE, NEURON CULTIVATING METHOD, CULTIVATED NEURON, ANALYSIS AND IDENTIFICATION OF PROTEIN IN AXON BUNDLE, AND USAGE OF CULTIVATED NEURON

(71) Applicant: THE FOUNDATION FOR THE PROMOTION OF INDUSTRIAL SCIENCE, Tokyo (JP)

(72) Inventors: Teruo Fujii, Tokyo (JP); Yoshiho Ikeuchi, Tokyo (JP); Shohei Kaneda, Tokyo (JP); Jiro Kawada, Tokyo (JP)

(73) Assignee: THE FOUNDATION FOR THE PROMOTION OF INDUSTRIAL SCIENCE, Tokyo (JP)

( * ) Notice: Subject to any disclaimer, the term of this patent is extended or adjusted under 35 U.S.C. 154(b) by 13 days.

(21) Appl. No.: 16/094,296

(22) PCT Filed: Feb. 1, 2017

(86) PCT No.: PCT/JP2017/003653
§ 371 (c)(1),
(2) Date: Oct. 17, 2018

(87) PCT Pub. No.: WO2017/187696
PCT Pub. Date: Nov. 2, 2017

(65) Prior Publication Data
US 2019/0127672 A1 May 2, 2019

Related U.S. Application Data

(60) Provisional application No. 62/328,905, filed on Apr. 28, 2016.

(51) Int. Cl.
| | |
|---|---|
| *C12M 3/00* | (2006.01) |
| *C12Q 1/02* | (2006.01) |
| *C12M 1/32* | (2006.01) |
| *C12M 1/12* | (2006.01) |
| *C12N 5/0793* | (2010.01) |
| *C12N 5/077* | (2010.01) |
| *G01N 33/50* | (2006.01) |

(52) U.S. Cl.
CPC .............. *C12M 21/08* (2013.01); *C12M 3/00* (2013.01); *C12M 23/12* (2013.01); *C12M 23/44* (2013.01); *C12M 37/04* (2013.01); *C12N 5/0619* (2013.01); *C12N 5/0658* (2013.01); *C12Q 1/02* (2013.01); *G01N 33/5005* (2013.01)

(58) Field of Classification Search
None
See application file for complete search history.

(56) References Cited

U.S. PATENT DOCUMENTS

2015/0219622 A1  8/2015  Hickman

FOREIGN PATENT DOCUMENTS

| JP | 2014-110804 A | 6/2014 |
| JP | 2015-524674 A | 8/2015 |
| WO | WO2016_040961 A1 | 3/2016 |

OTHER PUBLICATIONS

Mahmood et al (N Am J Me Sci 4: 429-434, 2012).*
Zeng et al, (SCTM 3: 1418-1428, 2014).*
Demestre et al, (Stem Cell Res 15: 328-336, 2015).*
Southam et al (J Neurosc Meth 218: 164-169, 2013).*
International Search Report in corresponding International Application No. PCT/JP2017/003653 filed Mar. 24, 2017.
Jeong, G.S. et al., Networked neural spheroid by neuro-bundle mimicking nervous system created by topology effect. Molecular Brain, 2015, vol. 8, No. 17, pp. 1-11, DOI: 10.1186/s13041-015-0109-y entire text, particularly, abstract, fig. 1, 2.
Kato-Negishi M. et al., A neurospheroid network-stamping method for neural transplantation to the brain. Biomaterials, 2010, vol. 31, pp. 8939-8945.
Srinivasan A. et al., Microchannel-based regenerative scaffold for chronic peripheral nerve interfacing in amputees. Biomaterials, 2015, vol. 41, pp. 151-165.

* cited by examiner

*Primary Examiner* — Daniel E Kolker
*Assistant Examiner* — Aditi Dutt
(74) *Attorney, Agent, or Firm* — Bacon & Thomas, PLLC

(57) ABSTRACT

An object is to provide a neuron cultivation device which promptly develops bundles of axons extending from neurons in vitro. A device for cultivating neuron with axon, the device comprising a cultivation plate and a plurality of modules arranged in the cultivation plate. Each of the modules includes at least one of first chambers receivable of cell bodies of neurons at least one of second chambers, and at least one of channels receivable of a bundle of axon extended from the cell bodies. The channels connect the first chambers and the second chambers. Bottom ends of the first chambers, the second chambers and the channels are closed and top ends of the first chambers and the second chambers are open.

15 Claims, 30 Drawing Sheets

NEURON CULTIVATION DEVICE, NEURON CULTIVATING METHOD, CULTIVATED NEURON, ANALYSIS AND IDENTIFICATION OF PROTEIN IN AXON BUNDLE, AND USAGE OF CULTIVATED NEURON

TECHNICAL FIELD

The present disclosure generally relates to a neuron cultivation device, a neuron cultivating method, cultivated neurons, an analysis and an identification of proteins in axon bundles, and usages of cultivated neurons.

BACKGROUND ART

It is necessary to cultivate neurons end axons in vitro for developing promptly pharmaceutical products effective against neurological disorders. Hitherto, some devices for cultivating neurons and axons have been proposed (see, NPL 1 and PTL 1). These devices are microfluidic culture platforms with plural compartments and enable to promote axonal growth to isolate axons.

CITATION LIST

Non Patent Literature

NPL 1: Taylor, Anne M et al, "A Microfluidic Culture Platform for CNS Axonal Injury, Regeneration and Transport" Nature methods 2.8 (2005): 599-605, PMC. Web. 8 Mar. 2016.

Patent Literature

PTL 1: US 2004/0106192 A1

SUMMARY OF INVENTION

Technical Problem

However, the aforementioned approaches do not give full satisfaction. For a precise evaluation of neural tissue in such a case of drug-screening, although it is necessary to evaluate respectively cell bodies, axons and conjugate portions of cell bodies and axons, any of aforementioned approaches cannot realize isolating each of them spatially and evaluating them.

One potential benefit of the current disclosure is that it can provide a neuron cultivation device which promptly develops bundles of axons extender from neurons in vitro.

Solution to Problem

The depicted embodiment includes a device for cultivating neuron with axon, the device comprising: a cultivation plate; and a plurality of modules arranged in the cultivation plate, each of the modules including at least one of first chambers receivable of cell bodies of neurons, at least one of second chambers, and at least one of channels receivable of a bundle of axon extended from the cell bodies, the channels connecting the first chambers and the second chambers, wherein bottom ends of the first chambers, the second chambers and the channels axe closed and top ends of the first chambers and the second chambers are open.

In another embodiment of the device, culture fluid is received in the first chambers, the second chambers and the channels, the top ends of the second chambers are closed by at least one of seal members.

In yet another embodiment of the device, the second chambers are receivable of skeletal muscles, so that the bundle of axon extended from the cell body conjugates with the skeletal muscles.

In yet another embodiment of the device, the channels are 100-150 [μm] width and 100-200 [μm] in height.

The another depicted embodiment includes a method for cultivating neuron with axon, the method comprising steps of applying cultivation fluid in at least one of first chambers, at least one of second chambers, and at least one of channels connecting the first chambers and the second chambers, the first chambers, the second chambers and channels included in at least one of modules arranged in a cultivation plate; inoculating neurons in the first chambers; and cultivating the neurons, so that a bundle of axons grows and extends in each of the channels.

In another embodiment of the method, skeletal muscle is inoculated in at least one of the second cha there, so that the bundle of axon extended from the neurons conjugates with the skeletal muscle.

The another depicted embodiment includes a plurality of neurons cultivated by inoculating in cultivation fluid, the neurons comprising cell bodies and at least one of bundles of axon extended from the cell bodies in predetermined directions.

In another embodiment of the neurons, the cell bodies, the bundles of axons and axon terminals are spatially isolated.

In yet another embodiment of the neurons, the neurons are in form of spheroid, the bundles of axons are expandable.

In yet another embodiment of the neurons, the bundles of axons conjugate with skeletal muscles.

In yet another embodiment of the neurons, the neurons comprising cell bodies and at least one of bundles of axon extended from the cell bodies in predetermined directions, the bundles of axon include cell body.

The another depicted embodiment includes a method of analyzing and identifying proteins in bundles of axons, the method comprising steps of cultivating neurons so that at least one of bundles of axons grows and extends from cell bodies of the neurons; and confirming by Western blotting that markers for indicating existence of the cell bodies are negative in the bundles of axons.

In another embodiment of the method, the markers are Map 2 and Nucleoporin.

In yet another embodiment includes a method of analyzing and identifying proteins in bundles of axons, the method comprising steps of: cultivating neurons so that at least one of bundles of axons grows and extends from cell bodies of the neurons; slicing the bundles of axons; and analyzing and identifying protein existing in the bundles of axons.

In yet another embodiment includes a method of using neurons including bundles of axons, the method comprising steps of: cultivating neurons so that at least one of bundles of axons grows and extends from cell bodies of the neurons; applying fluorescent treatment to the neurons; and providing KCl to the cell bodies so as to observe electrophysiologically activity.

Effect of Invention

According to the present disclosure, it is possible to promptly develop bundles of axons extending from neurons in vitro.

BRIEF DESCRIPTION OF DRAWINGS

FIGS. 6A(a)-6A(b) are another set of photographs showing axons grown in channels of the cultivation plate.

FIG. 17A is a view of graph showing a result of evaluating orientation of an axon in stress test.

DESCRIPTION OF EMBODIMENTS

An embodiment will now be described in detail with reference to the drawings.

Figure 1:
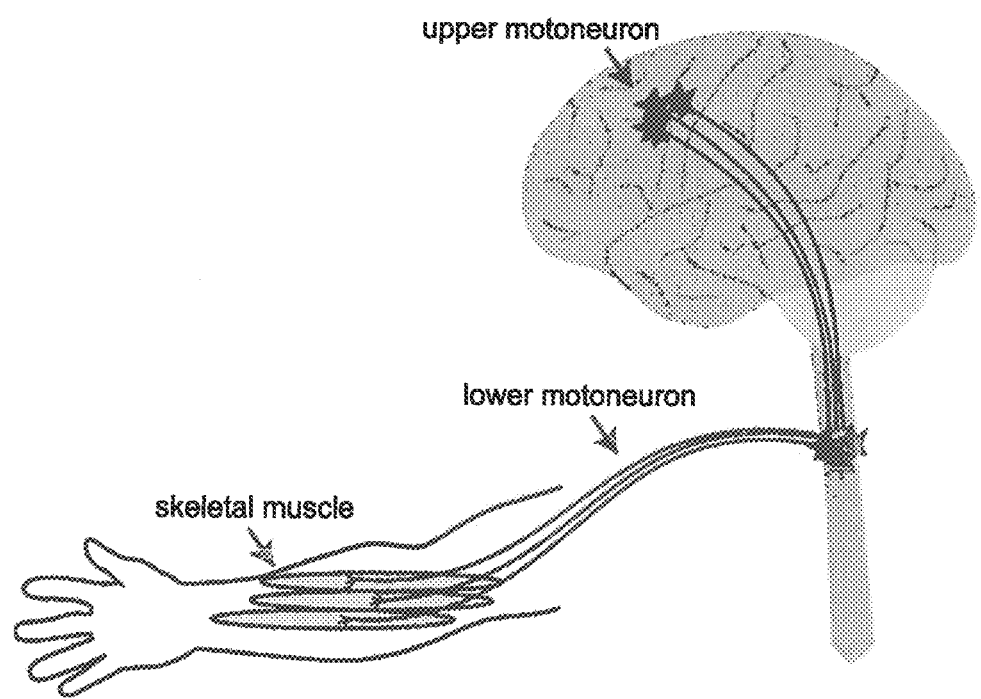
FIG. 1 is a schematic view showing a back ground.
Figure 2:
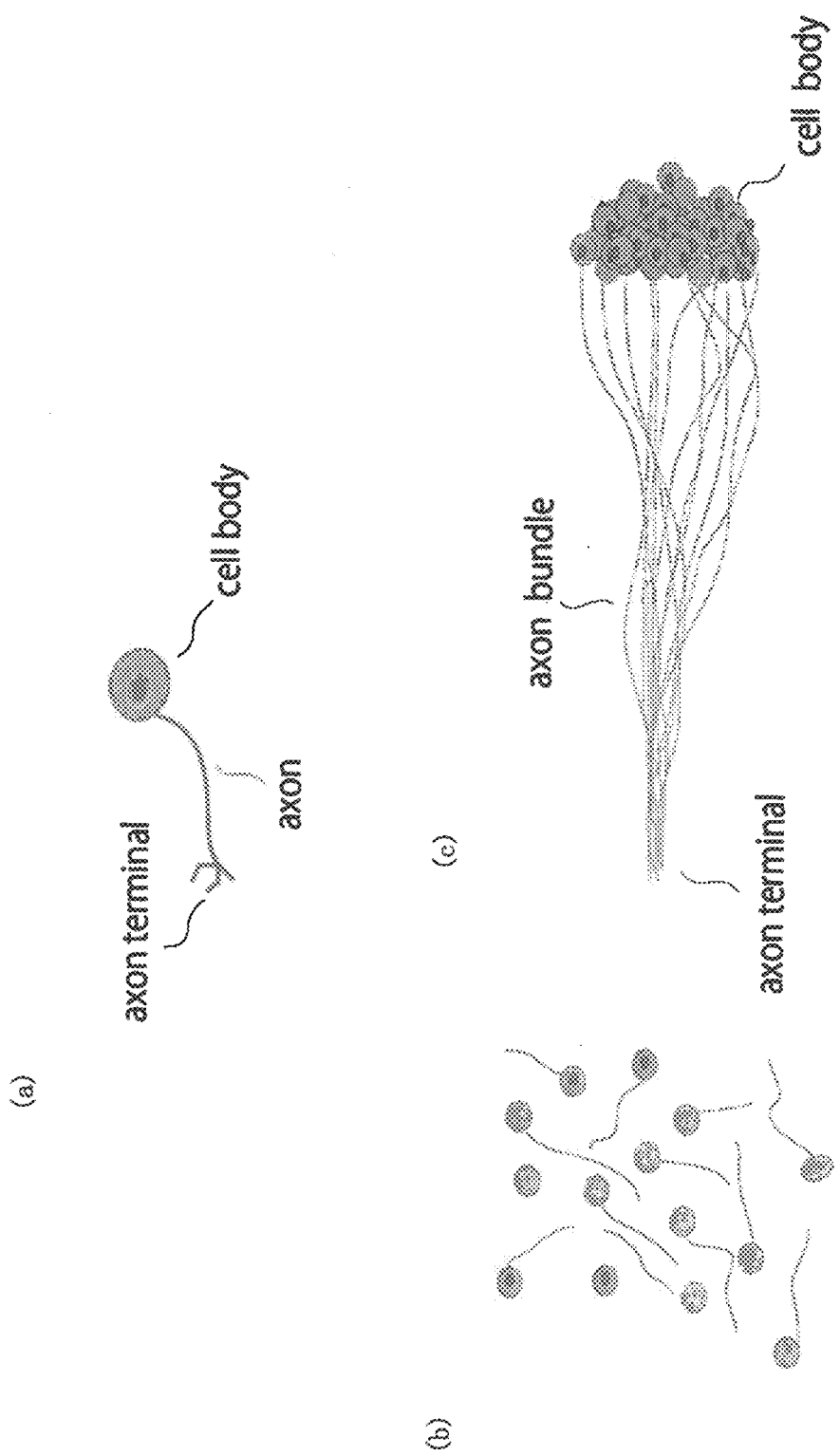
FIGS. 2(a)-2(c) are a set of views showing general concepts.

FIG. 1 is a schematic view showing a hack ground. FIG. 2 is a set of views showing general concepts. In FIG. 2, (a) shows a schematic view of a neuron, (b) shows a result of conventional cultivation, (c) shows a concept of the present embodiment.

The present embodiment proposes a new process of cultivation of neuron with axon, a new device suitable for cultivation and a cultivated mass of neurons with a bundle of axons. For researching promptly pharmaceutical products effective against neurological disorders, it is important to cultivate neurons in an environment similar to that in a body system. A neuron comprises a cell body and an axon with an axon terminal, as shown in FIG. 2. And, as shown in FIG. 1, axons of motoneurons are bundled in a body system, and axon terminals conjugate with plural skeletal muscle cells. Thus, it is desirable to generate a mass of cell bodies or a cell body spheroid with axons in a bundle in such a state that the cell bodies, axons and axon terminals are spatially isolated each other, as shown in FIG. 2 (c), through in vitro cultivation. For confirming appropriately effects of pharmaceutical products, it is necessary to apply the products to each of such portions as the cell bodies, axon bundle and axon terminals on evaluate, and to evaluate the effect of products on each of the portions. Though, conventional ways of cultivation could only provide cell bodies with axons in such a random state that cell bodies and axons are spatially mixed, as shown in FIG. 2(b).

Next will be described a fabrication of device used in the present embodiment.

Figure 3:
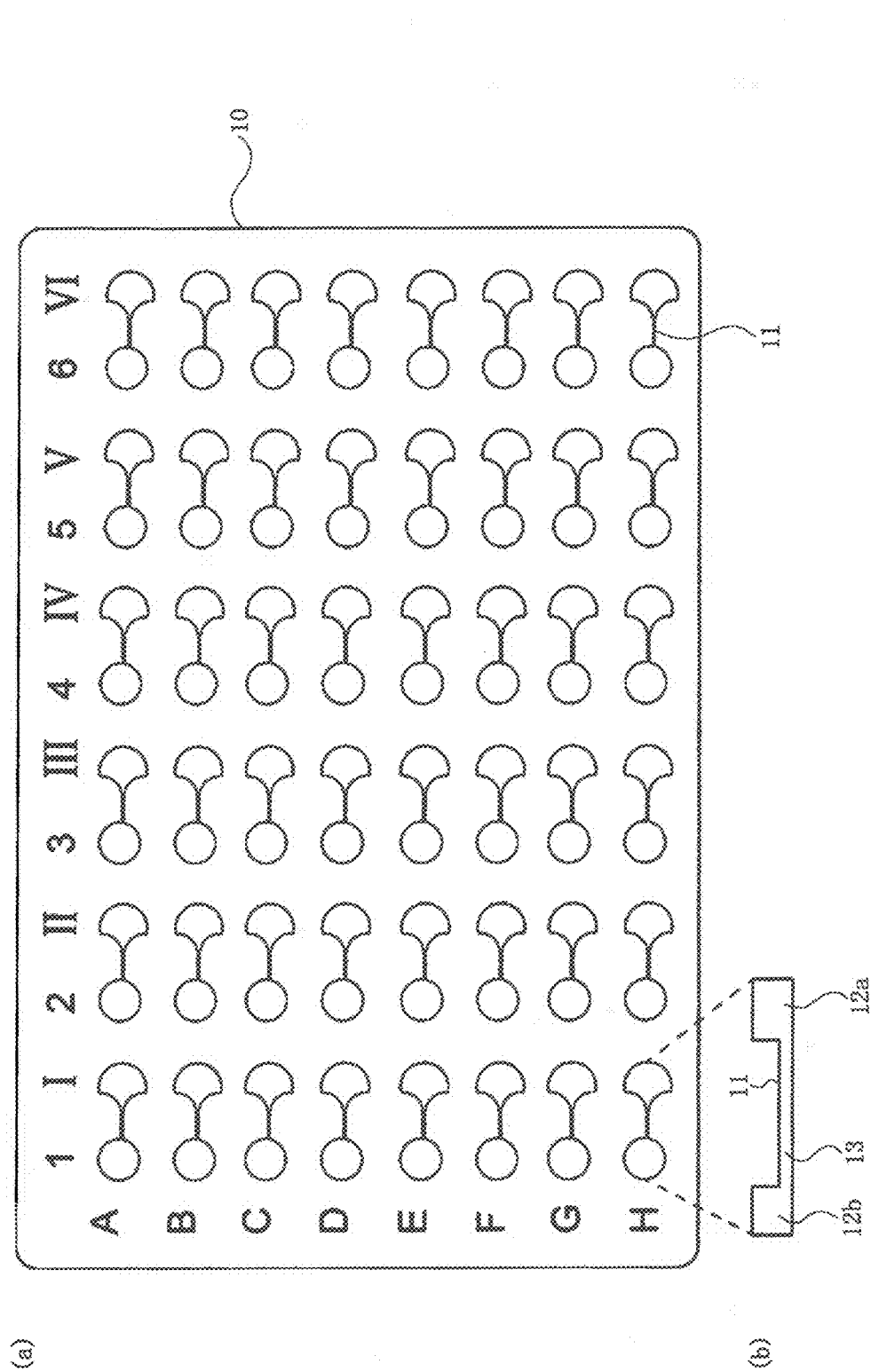
FIGS. 3(a)-3(b) are a set of views of a cultivation plate.
Figure 4:
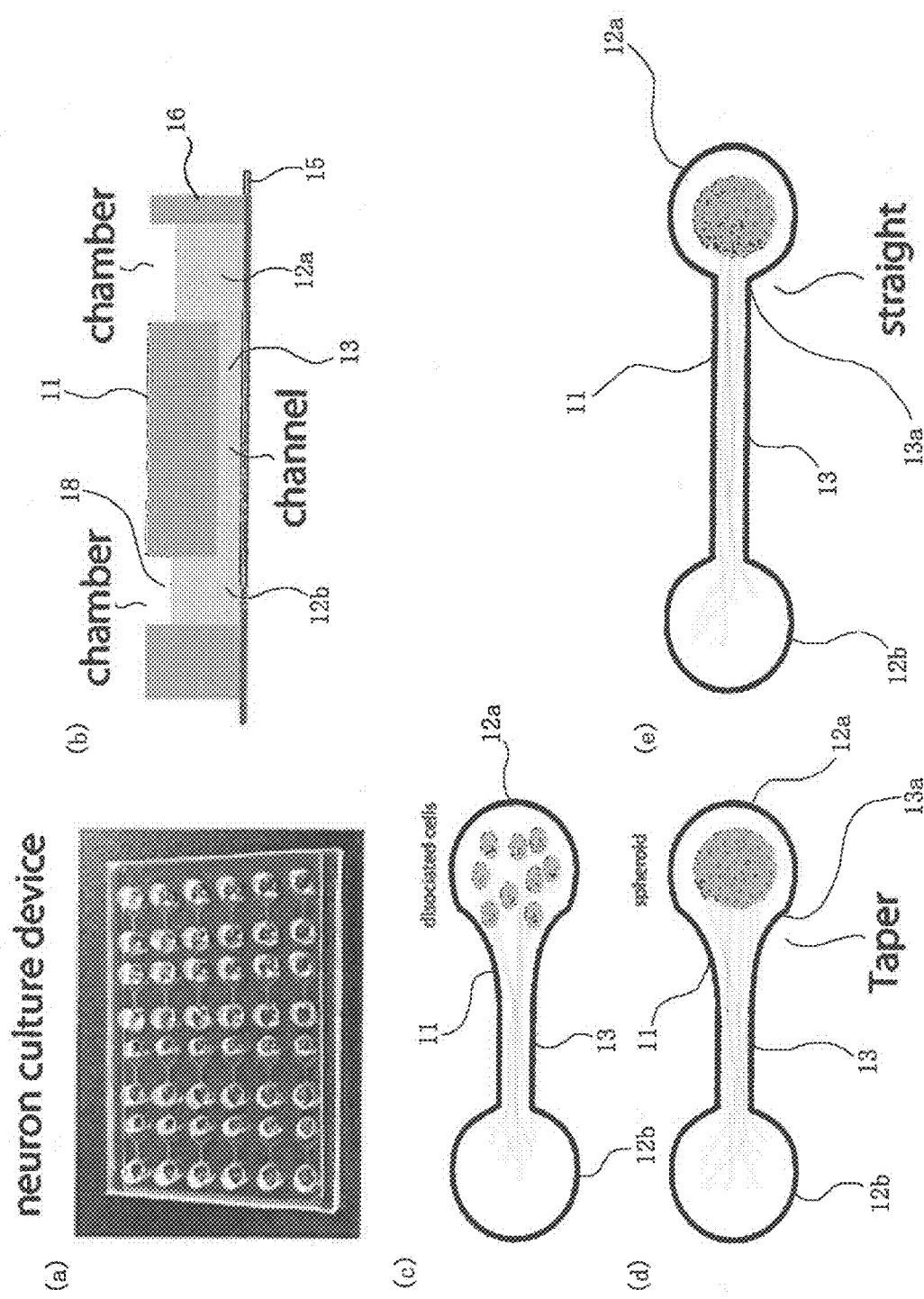
FIGS. 4(a)-4(e) are a set of views of a cultivation module in a cultivation plate.
Figure 5:
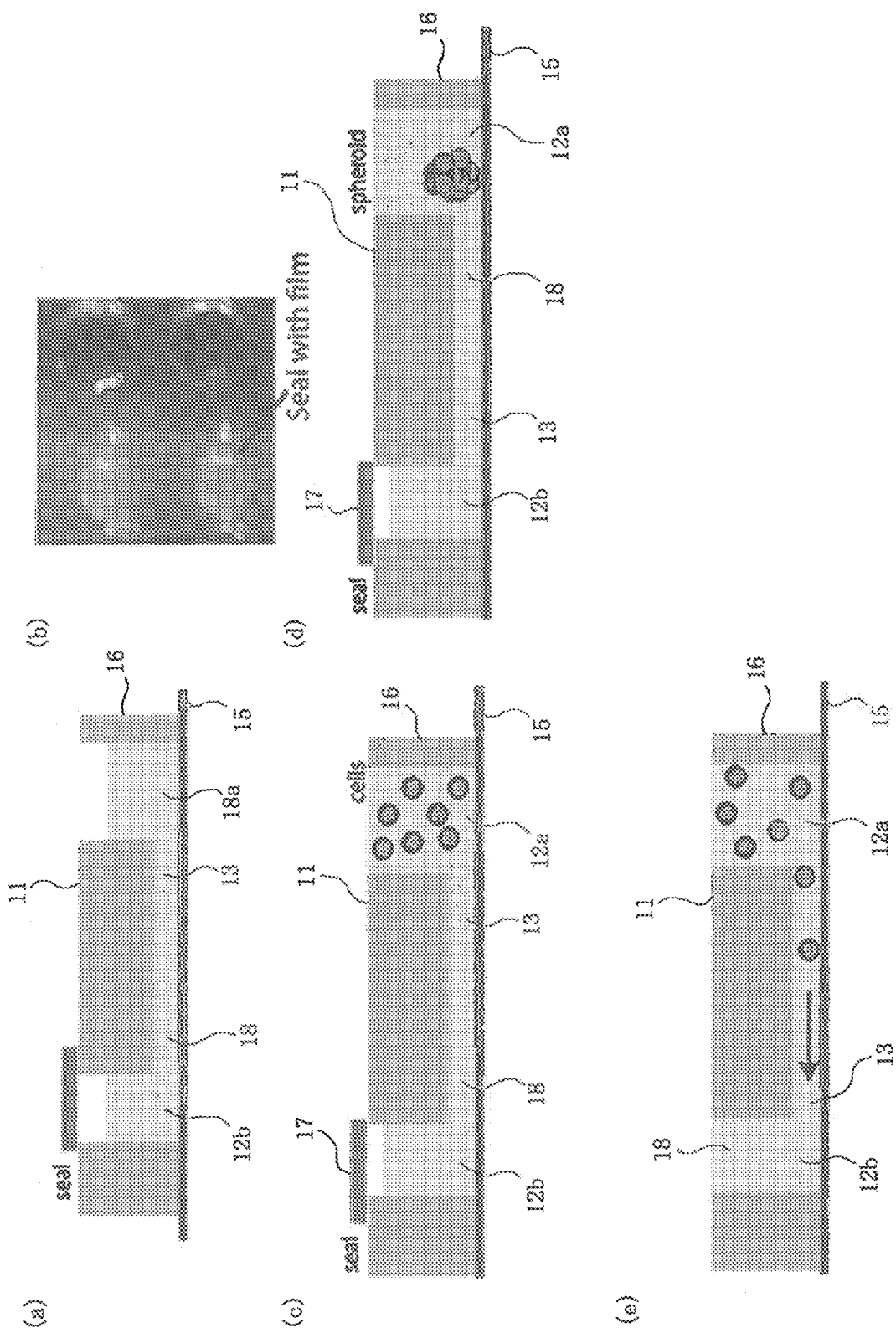
FIGS. 5(a)-5(e) are a set of views showing a cultivation module with a seal.

FIG. 3 is a set of views of a cultivation plate. FIG. 4 is a set of views of a cultivation module in a cultivation plate. FIG. 5 is a set of views showing a cultivation module with a seal. In FIG. 3, (a) is a plan view, (b) is an enlarged cross sectional view of a cultivation module in (a). In FIG. 4, (a) is a photograph of a cultivation plate, (b) is a schematic cross sectional view of a cultivation module, each of (c)-(e) is a schematic plan view of a cultivation module. In FIG. 5, (a) is schematic cross sectional view of a cultivation module with a seal, (b) is a photograph of a cultivation module with a seal, (c) as schematic cross sectional view of a cultivation module with a seal and cells, (d) is schematic cross sectional view of a cultivation module with a seal and a cell body spheroid, (e) is schematic cross sectional view of a cultivation module without a seal.

In the present embodiment, a cultivation plate 10 is employed. As shown in. FIGS. 3(a) and 4(a), the cultivation plate 10 is a plate of rectangular shape and includes a plurality of modules 11, which are configured in lines and in rows. And the cultivation plate 10 includes a base board 15 made of a coverslip, which is a transparent glass plate, and a top board 16 attached onto a surface of the base board 15. In the top board 16, a plurality of modules 11 are formed. As shown in FIGS. 3 and 4, each module 11 has a shape like a dumbbell in a plan view and a shape like the letter "U" as a whole in a sectional view, and includes a first chamber 12a, a second Chamber 12b and a channel 13 connecting the bottoms of the first and second chambers 12a, 12b.

The top board 16 can be a PDMS (poly-dimethyl-siloxane) sheet and can be produced with utilizing a known photolithographic technology (see, for example, NPL 1 and PTL 1). The top board 16 may be replaced by a sheet made of other polymers or glasses, such as Pyrex®, etc. or also may be fabricated by other methods, such as hot embossing, drilling, etc.

Each of the first and second chambers 12a, 12b is a cylindrical concave and is constructed as a well, a bottom end of which is closed by the base board 15 and a top end of which is open. One end of the channel 13 is opened in a bottom end of a side wall of the first chamber 12a and the opposite end of it is opened in a bottom end of a side wall of the second chamber 12b. The width of the channel 13 is preferably 100-150 [μm] and the height is preferably 100-200 [μm], though these measurements are not limited to these figures but can be arranged if necessary And inside the first and second chambers 12a, 12b and the channel 13, culture fluid 18 is Red. The structure of the module 11 is so simple that the culture fluid 18 can smoothly flow therein. Also, the size of the channel 13 is so large, as compared with those of the conventional devices (see, for example, NPL 1 and PTL 1), that the culture fluid 18 in both chambers 12a, 12b can be mixed naturally. A plan view shape of each of first and second chambers 12a, 12b is preferably a true circle as shown in FIG. 4(e), though it is not limited to the true circle but can be arranged if necessary According to examples shown in FIGS. 3(a), 4(c) and (d), the plan view shape of the first chamber 12a is not of a true circle but of a deformed one since an entrance part 13a of the channel 13 has a tapered shape, while that of the second chamber 12b is of a nearly true circle since the entrance part 13a of the channel 13 has a straight shape. When the entrance part 13a has a tapered shape, the axons can be guided into the channel 13 effectively Even when the entrance part 13a has a straight shape, the axons can form a bundle in the channel 13.

In one of the chambers 12a, 12b, cell bodies of neurons are disposed or inoculated. While either one can be selected as a chamber for inoculating the cell bodies therein, for the sale of convenience, the first chamber 12a is considered as the chamber for inoculating the cell bodies in this embodiment. In an example shown in FIG. 4(c), plural neuron cell bodies are inoculated separately or in a state of dissociated cells. And in an example shown in FIGS. 4(d) and (e), plural neuron cell bodies are inoculated in a mass or in a state of spheroid. Then after a while of cultivation, axons of neurons extend in the cannel 13 to the second chamber 12b and form a bundle in the channel 13. Preferably the bore of the Channel 13 is large enough to receive a bundle of axons of neurons.

As shown in FIGS. 5(a) and (b), it is preferable to put a seal member 17 on the second chamber 12h, in which any of neuron cell body is not inoculated, so as to close its open end. The seal member 17 is preferably made of PCR (Polymerase Chain Reaction) sealing plate or sealing film, though it is not limited to this but can be made of any kind of material suitable for sealing. It would be easier to inoculate and keep the neuron cell bodies in the first chamber 12a, as shown in FIGS. 5(c) and (d), when the open end of the second chamber 12b is closed by the seal member 17, since the culture fluid 18 is hindered from flowing into the second chamber 12b. When the open end of the second chamber 12b is kept open as shown in. FIG. 5(e), the neuron cell bodies disposed in the first chamber 12a tend to flow into the second chamber 12b with the culture fluid 18. If the neuron cell bodies in a state of spheroid are inoculated in the first chamber 12a, the seal member 17 can be omitted, since the cell body spheroid is too large to flow in the channel 13.

Next will be described results of experiments for growing axons accomplished by the present inventors using the cultivation plate 10 according to the present embodiment.

Figure 6:
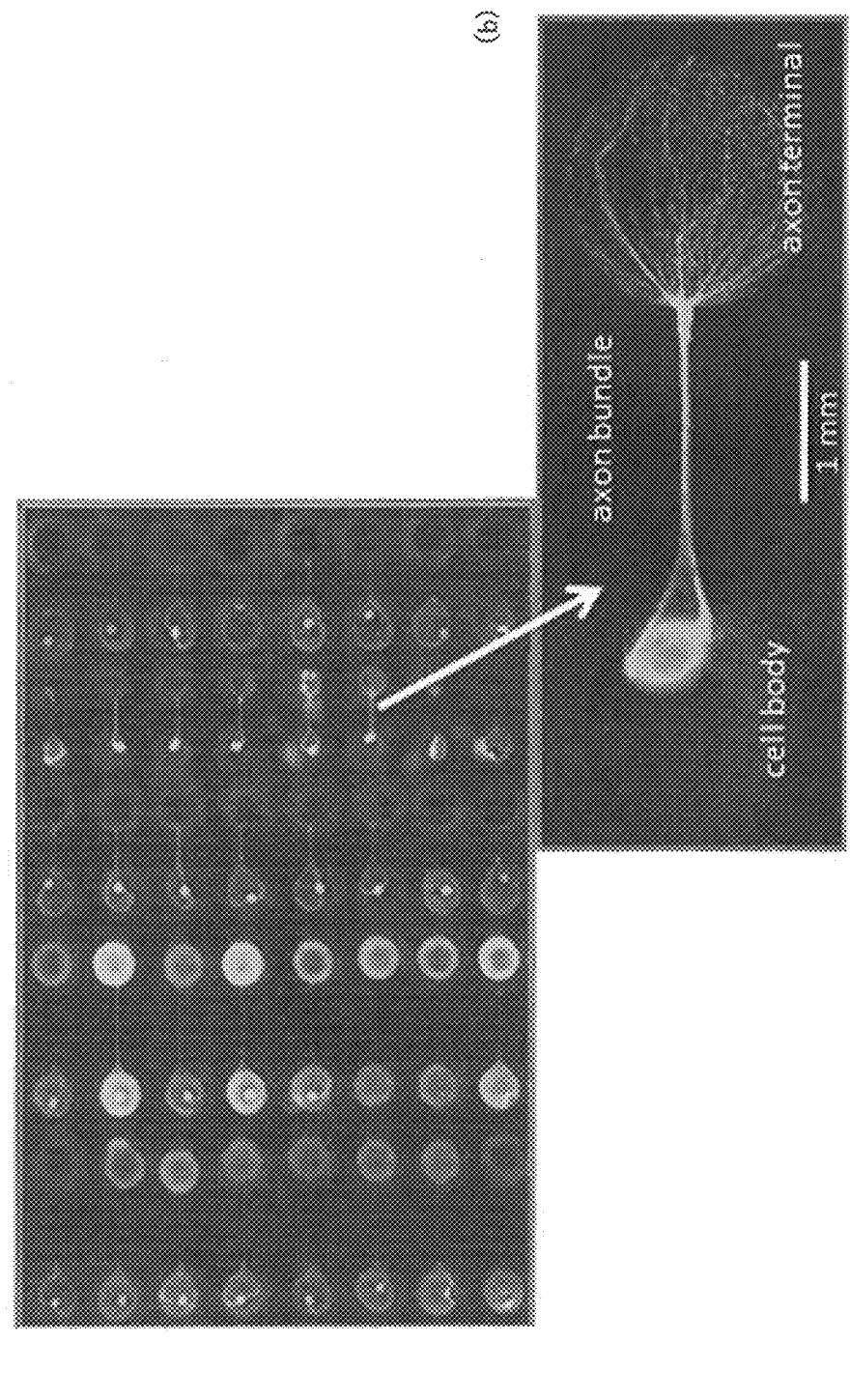
FIGS. 6(a)-6(b) are a set of photographs showing axons grown in channels of the cultivation plate.
Figure 6A:
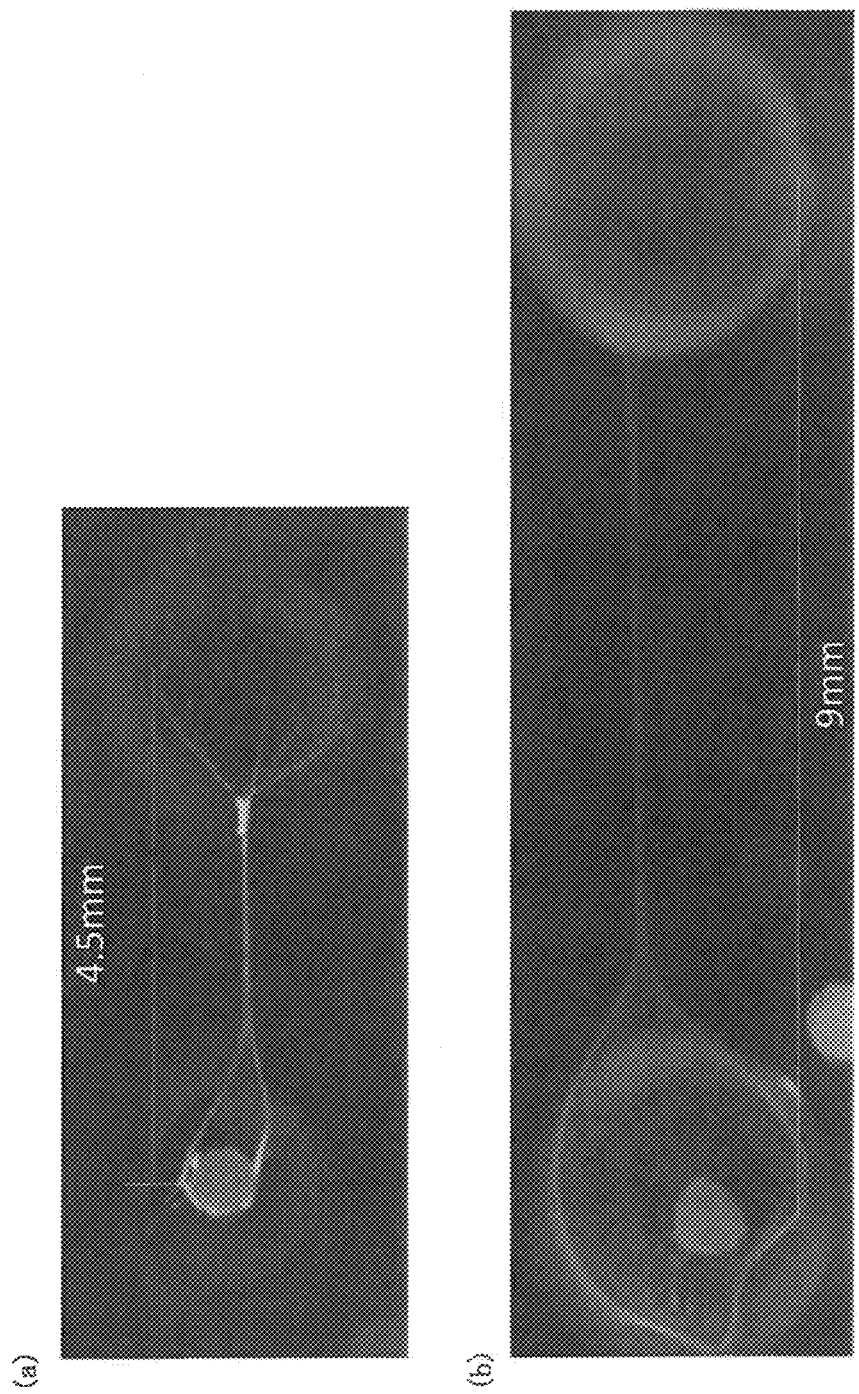
Figure 7:
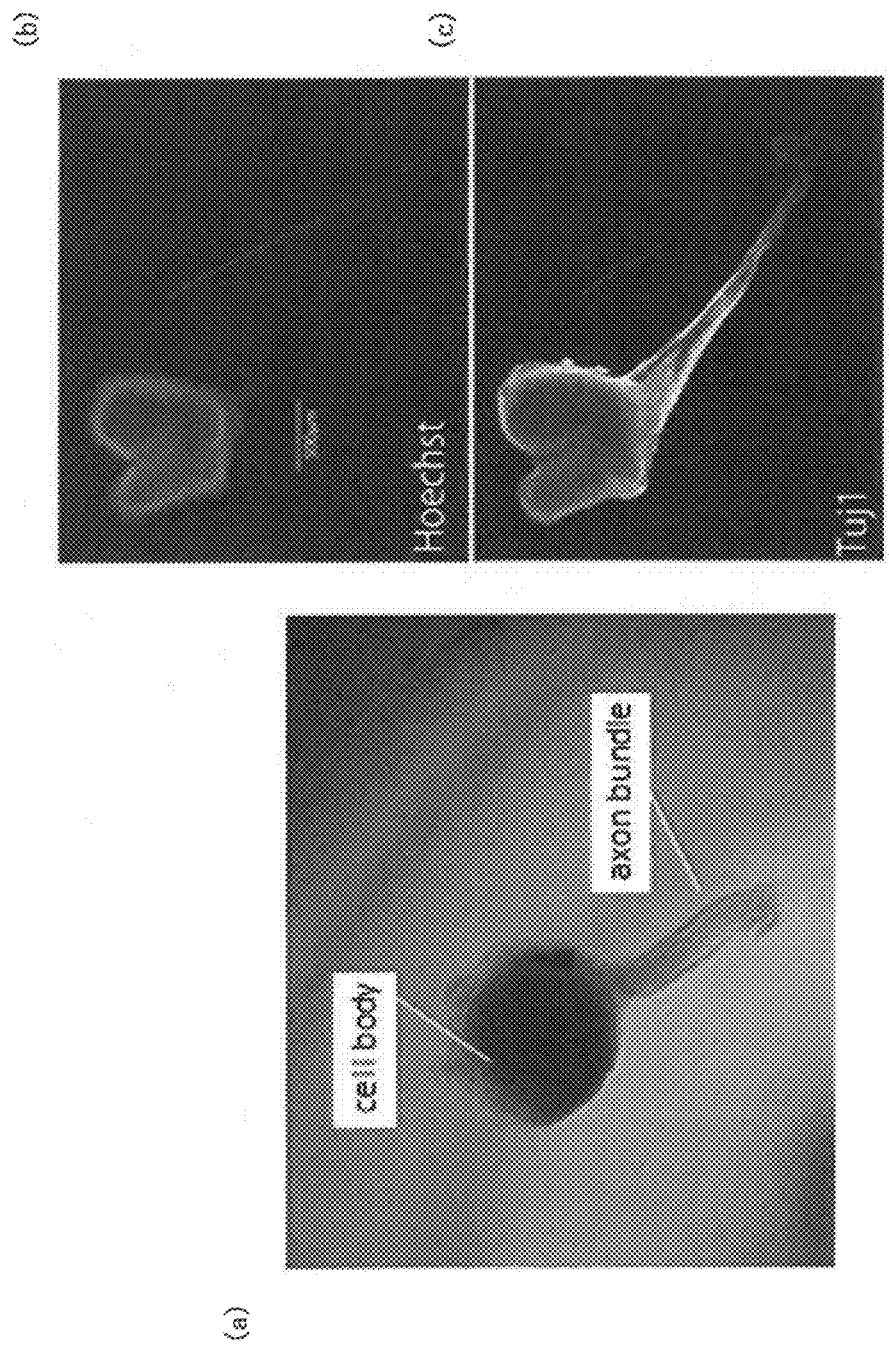
FIGS. 7(a)-7(c) are a set of photographs showing axons extracted from the cultivation plate.

FIG. 6 is a set of photographs of showing axons grown in channels of the cultivation plate. FIG. 6A is another set of photographs showing axons grown in channels of the cultivation plate. FIG. 7 is a set of photographs showing axons extracted from the cultivation plate. In FIG. 6, (a) is a photograph of a part of the cultivation plate, (b) is an enlarged photograph of axons in one of the modules shown in (a). In FIG. 6A, (a) is a photograph of an example with an axon 4.5 [mm] in length, (b) is a photograph of an example with an axon 9 [mm] in length. In FIG. 7, (a) is an enlarged photograph of neural tissue, (b) is a fluorescent image of cell nucleoli (Hoechst), (c) is a fluorescent image of the whole neurons (Tuj1).

In the present experiments, motoneurons derived from human iPS cells (409B2 cell lines) were used. The cell body spheroids of the motoneurons were inoculated in the first chambers 12a and cultivated. The motoneurons were gained from human iPS cells by using a well plate or a dish. And the cell spheroids were gained by using a non-adherent cultivation plate. Further, the cultivation was accomplished under the environment of 37[° C.], $O_2$:20 [%], $CO_2$: 5 [%]. Then, as shown in FIG. 6, axons grew and extended in the cannels 13 to the second chambers 12b. After cultivation, the aggregated motoneurons were extracted or brought out from the modules 11 of the cultivation plate 10. The aggregated motoneurons extracted from the modules 11 had a large axon bundle extended from the aggregated cell bodies, as shown in FIG. 7(a). Cell nucleoli, which were in the cell bodies and were stained with a marker, Hoechst, were sighted in the aggregated motoneurons, as shown in FIG. 7(b). And the aggregated motoneurons, which were stained with a marker, Tuj1, as a whole, were sighted, as shown in FIG. 7(c). The axon bundle was clearly recognized as extending from the aggregated cell bodies. A variety sizes of axon bundle can be obtained by changing the length and the bore of channel 13. For instance, the length of the axon is 4.5 [mm] in an example shown in FIG. 6A(a) and 9 [mm] in an example shown in FIG. 6A(b). It is preferably not less than 1 [mm] for the use of observation or experiment. The width of axon bundle can be 100 [μm], for example. In this case, about 5500 of axons are found in a cross section of the bundle by TEM image observation, as shown later in FIG. 20(c).

As mentioned above, ac cording to the present embodiment, an axon bundle can be obtained through cultivation in each of the plural modules 11 of the cultivation plate 10. Therefore, screening pharmaceutical products can be speedily accomplished by applying the products to the axon bundle in each of the plural modules 11. Further, since the axon bundle is isolated from the cell bodies in each module 11, pharmaceutical products effective against neurological disorders can be screened by applying the products accurately to the axon bundle in each module 11, and also it can be confirmed which part of the axon bundle the products effect in, such as in the distal end or the proximal end of the axon bundle.

Next will be described results of experiments on conjugation of axons and skeletal muscle accomplished by the present inventors using the cultivation plate 10 according to the present embodiment.

Figure 8:
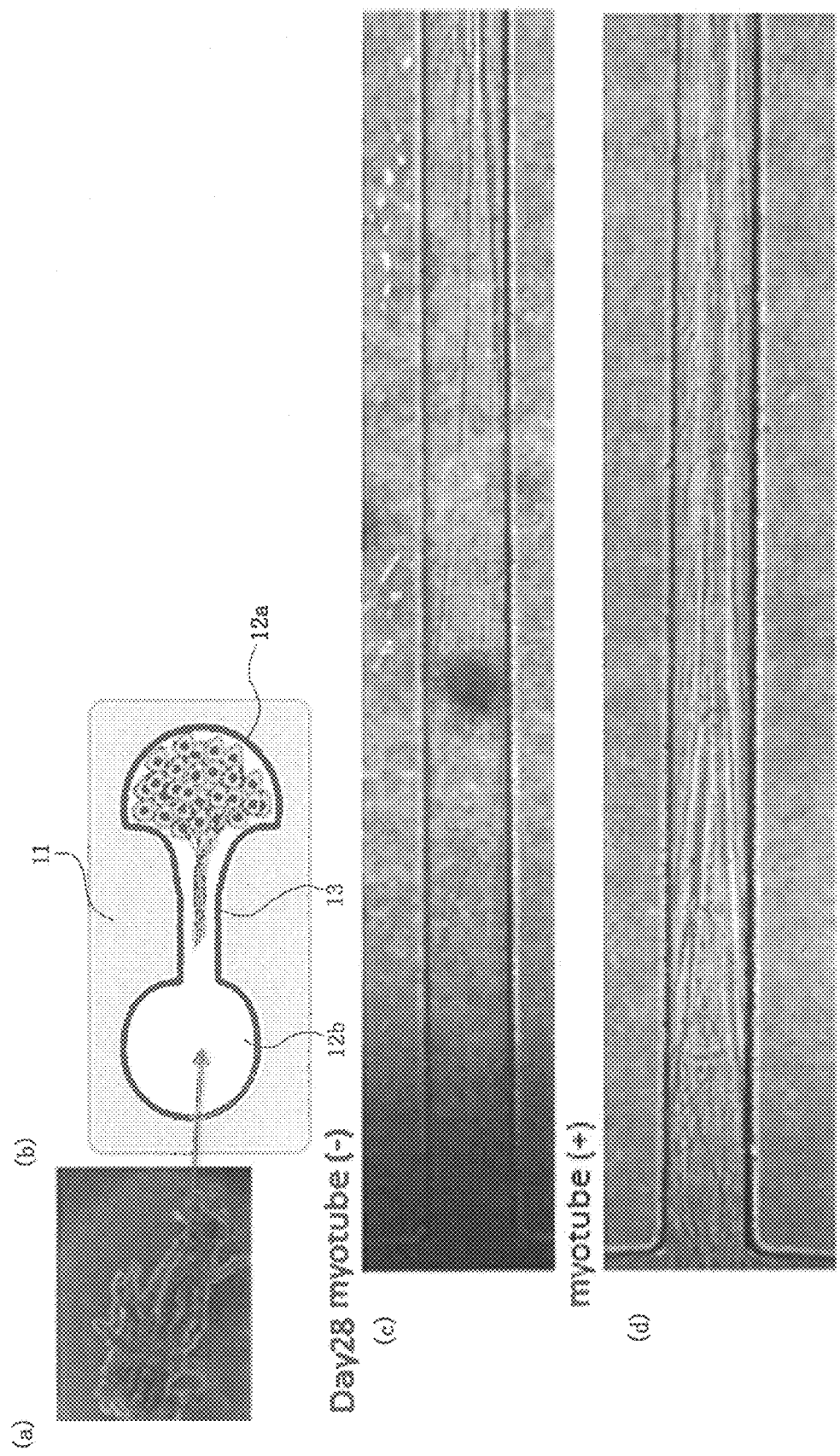
FIGS. 8(a)-8(d) are a set of views illustrating an experiment on conjugation of axons of motoneurons derived from 409B2 cell lines and skeletal muscle of laboratory mouse.
Figure 9:
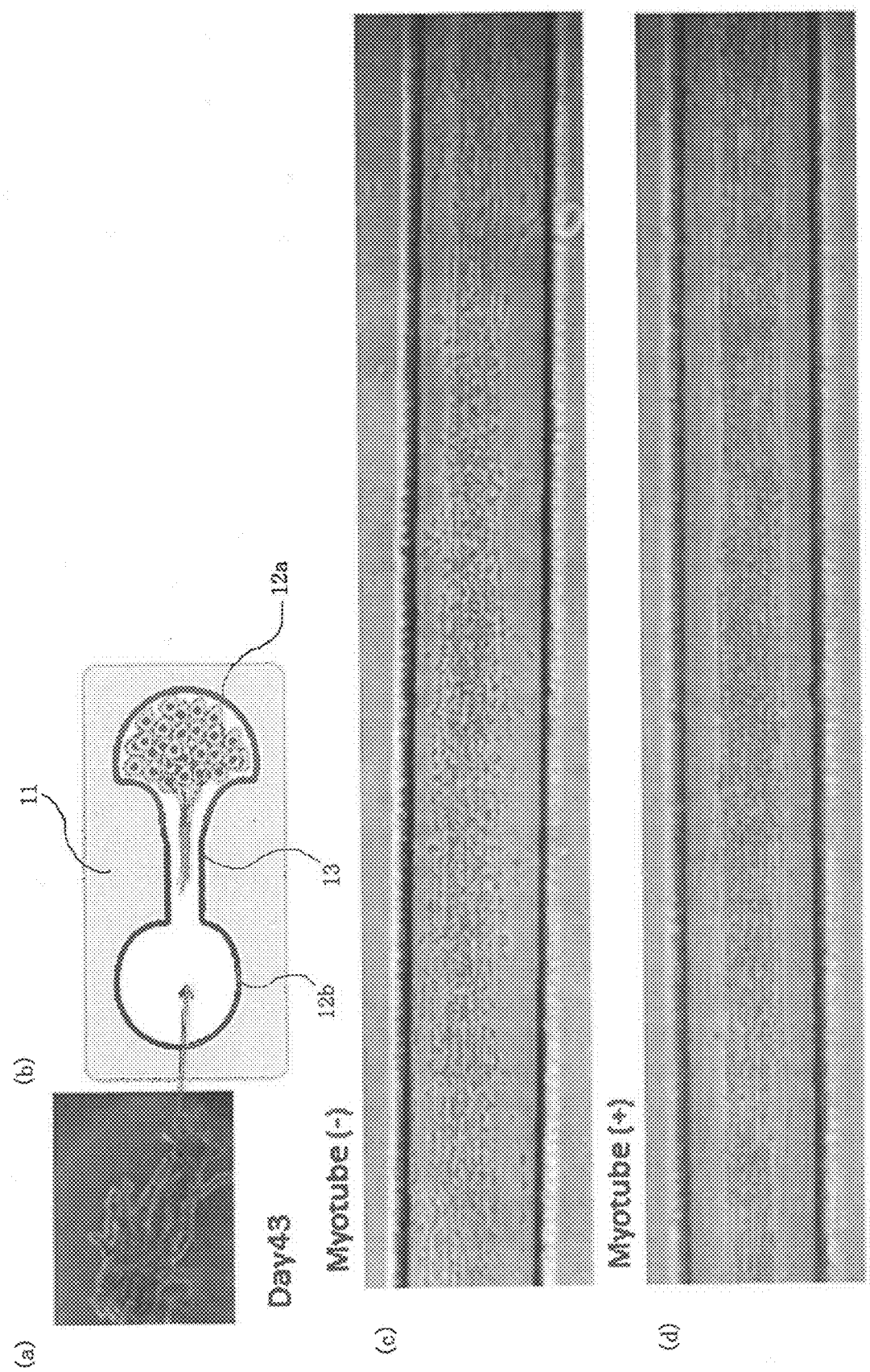
FIGS. 9(a)-9(d) are a set of views illustrating a long period experiment on conjugation of axons of motoneurons derived from 409B2 cell lines and skeletal muscle of laboratory mouse.
Figure 10:
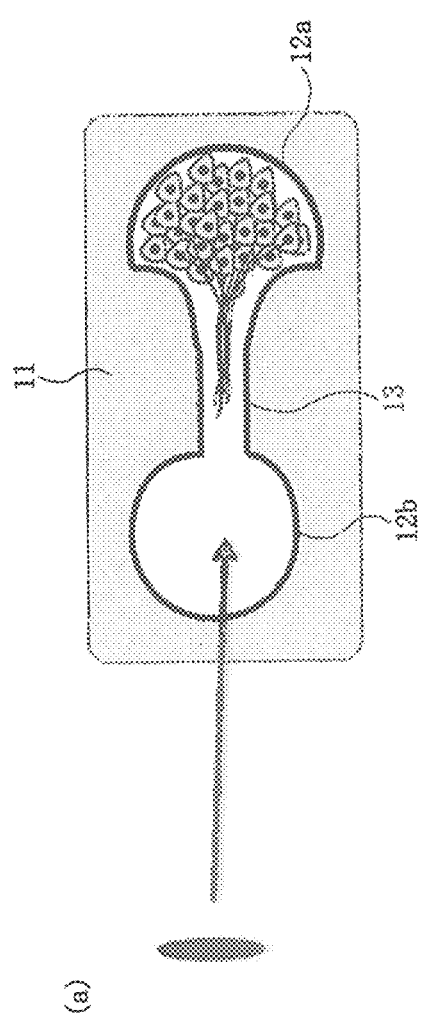
FIGS. 10(a)-10(b) are a set of views illustrating an experiment on conjugation of axons of motoneurons derived from 409B2 cell lines and skeletal muscles derived from C2C12 cell lines.
Figure 10:
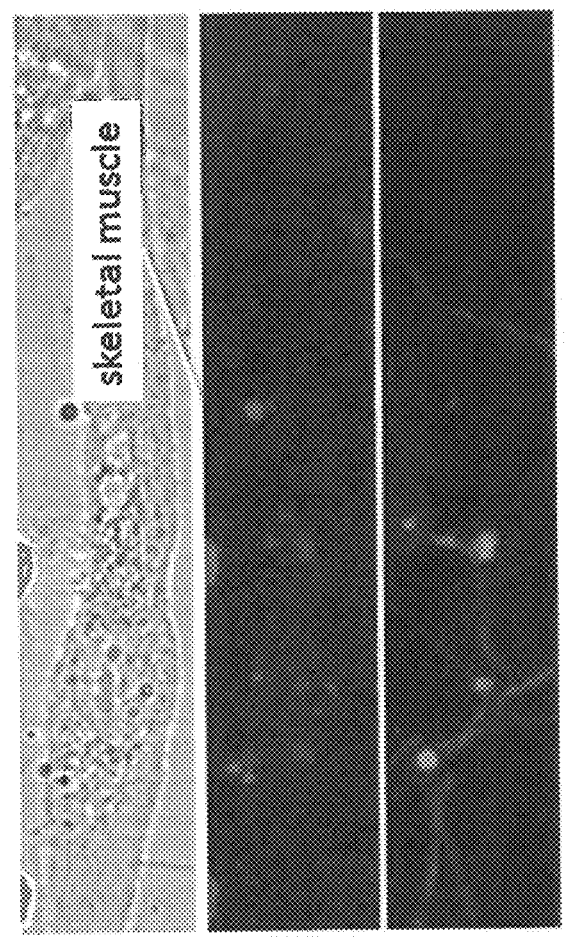

FIG. 8 is a set of views illustrating an experiment on conjugation of axons of motoneurons derived from 409B2 cell lines and skeletal muscle of laboratory mouse. FIG. 9 is a set of views illustrating a long period experiment on conjugation of axons of motoneurons derived from 409B2 cell lines and skeletal muscle of laboratory mouse. FIG. 10 is a set of views illustrating an experiment on conjugation of axons of motoneurons derived from 409B2 cell lines and skeletal muscles derived from C2C12 cell lines. In FIG. 8, (a) is a photograph of myotube of laboratory mouse, (b) is a schematic plan view of a module, (c) is an enlarged photograph of axons without myotubes, (d) is an enlarged photograph of axons with myotube. In FIG. 9, (a) is a photograph of myotube of Laboratory mouse, (b) is a schematic plan view of a module, (c) is an enlarged photograph of axons without myotubes, (d) is an enlarged photograph of axons with myotube. In FIG. 10, (a) is a schematic plan view of a module, (b) is an enlarged photograph of a part of conjugation.

In the first experiment, motoneurons derived from human iPS cells (409B2 cell lines) were used as the neurons and myotubes of laboratory mouse (shown in FIG. 8(a)) were used as the skeletal muscles. The motoneurons and the cell body spheroids were gained in the same way as mentioned above and the cultivation was accomplished in the same way as mentioned above. As shown in FIG. 8(b), the neurons were inoculated in the first chamber 12a and the skeletal muscles were inoculated in the second chamber 12b, then they were co-cultivated. It was found that the growth speed of axons was higher and the axon bundle grew thick sooner when the skeletal muscles were inoculated in the second chamber 12b than otherwise. FIGS. 8(c) and (d) show axons growing state in the channels 13 after 28 days of cultivation, respectively, in case that any myotube was not inoculated in the second chamber 12b and in case that myotubes were inoculated therein. In the second experiment, the co-cultivation was carried out in a longer period (43 days) than the first experiment (28 days) but in the same way using the same module 11 and the same motoneurons and myotubes as the first experiment, as shown in FIGS. 9(a) and (b). It was found that the shape of the axon bundle deformed when any myotube was not inoculated in the second chamber 12b. FIGS. 9(c) and (d) show axons growing state in the channels 13 after 43 days of cultivation, respectively, in case that any myotube was not inoculated in the second chamber 12b and in case that myotubes were inoculated therein.

In the third experiment, motoneurons derived from human iPS cells (409B2 cell lines) were used as the neurons and striated muscles derived from mouse myoblast cells (C2C12 cell lines) were used as the skeletal muscles. As shown in FIG. 10(a), the neurons were inoculated in the first chamber 12a and the skeletal muscles were inoculated in the second chamber 12b, then they were co-cultivated. Then a part of conjugation of axons and skeletal muscle was stained with α-Bungarotoxin, while the axons were stained with Tuj1. As shown in FIG. 10(b), conjugation of axons and skeletal muscle was sighted.

As mentioned above, according to the present embodiment, axon terminals can be conjugated with the skeletal muscles in the second chamber 12b apart from the first chamber 12a, in which the cell bodies exist. In other words, the present embodiment can provide a situation similar to that in a body system. Therefore, pharmaceutical products effective against neurological disorders can be screened by applying the products accurately to the conjugation of axons and, skeletal muscles in each module 11.

Next will be described a result of experiment for growing a bundle of axons accomplished by the present inventors using the cultivation plate 10 and slicing it to observe protein therein.

Figure 11:
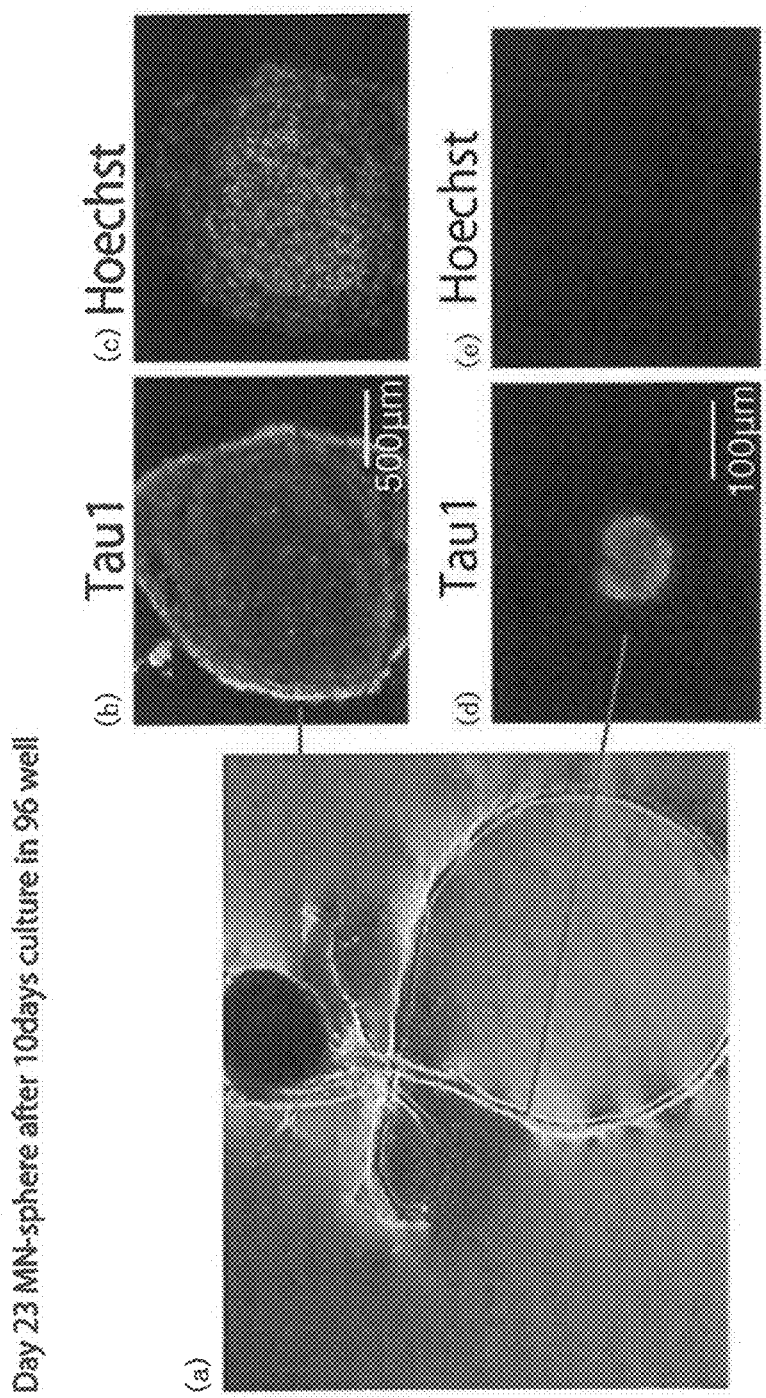
FIGS. 11(a)-11(e) are a set of photographs showing a bundle of axons used for protein observation.

FIG. 11 is a set of photographs of showing a bundle of axons used for protein observation. In FIG. 11, (a) is a photograph of a cell body spheroid with a bundle of axons extracted outside from the cultivation plate, (b) is a photograph showing existence of axon (Tau 1) in the spheroid shown in (a), (c) is a fluorescent image of cell nuclei (Hoechst) in the spheroid shown in (b), (d) is an enlarged photograph showing existence of axon in a slice of the bundle of axon shown in (a), (e) is a fluorescent image showing non-existence of cell nuclei shown in the slice of the bundle of axon.

In the present experiment, motoneurons derived from human iPS tells (409B2 cell lines) were used. The cell body spheroids of the motoneurons were inoculated in the first chambers 12a and cultivated. The motoneurons and the cell body spheroids were gained in the same way as mentioned above and the cultivation was accomplished in the same way as mentioned above. After 10 days of cultivation, one of the motoneurons including a well grown and extended bundle of axon was extracted or brought out from the module 11 of the cultivation plate 10, as shown in FIG. 11(a). Then the bundle of axon was sliced to get some slices suitable for observation of protein therein. As shown in FIG. 11(d), it was confirmed that protein appeared in the bundle of axon. Also, as shown in FIG. 11(e), it was confirmed that there was no cell nucleolus existing in the bundle of axon, so that the bundle was confirmed as a highly pure collection of axons.

As mentioned above, according to the present embodiment, a cell body spheroid integrated with a bundle of axon can be brought out from each of the modules 11 of the cultivation plate 10. Therefore, by slicing the bundle of axons and observing protein therein, it is possible to analyze and identify proteins existing in the bundle of axons, also it is possible to semen or identify neurological disorders, and, further, it is possible to screen pharmaceutical products effective against neurological disorders. On the other hand, any of conventional ways of motoneuron cultivation has not obtained cellular tissues with are aggregated cell bodies and an axon bundle integrated, so that it has been difficult to observe the inside each of the cell bodies and the axon bundle outside the conventional cultivation devices.

Next will be described a result of experiment for expanding a bundle of grown axons accomplished by the present inventors using the cultivation plate 10.

Figure 12:
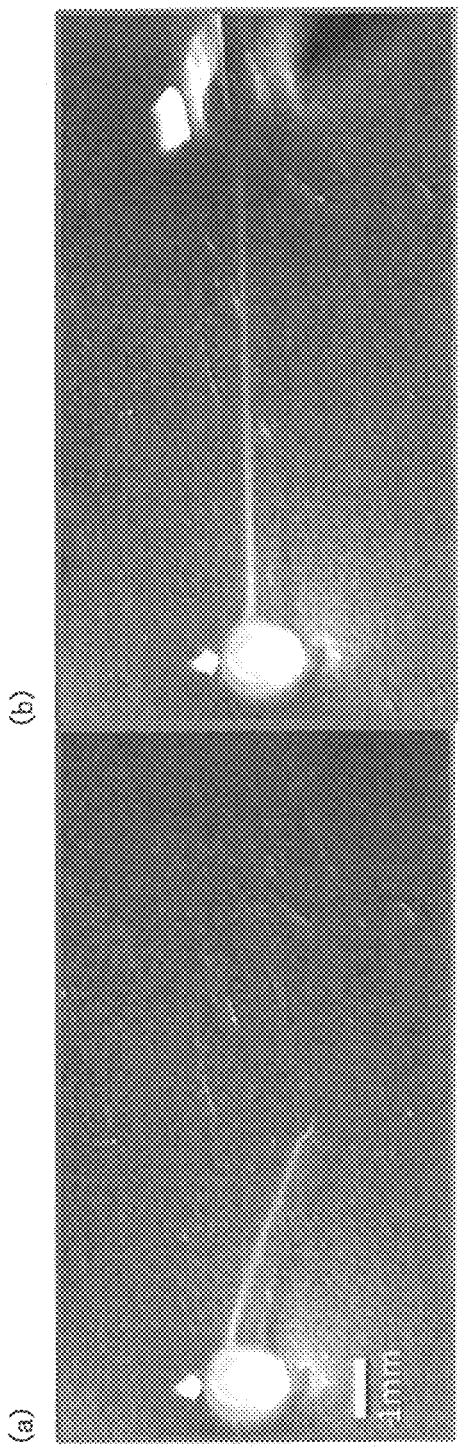
FIGS. 12(a)-12(b) are a set of photographs showing a bundle of axons used for expansion.

FIG. 12 is a set of photographs showing a bundle of axons used for expansion in FIG. 12, (a) is a photograph of a spheroid with a bundle of axons outside the cultivation plate before expansion, (b) is a photograph of a spheroid with a bundle of axons outside the cultivation plate after expansion.

In the present experiment, motoneurons derived from human iPS cells (409B2 cell lines) were used. The cell spheroids of the motoneurons were inoculated in the first chambers 12a and cultivated. The motoneurons and the cell spheroids were gained in the same way as mentioned above and the cultivation was accomplished in the same way as mentioned above. After cultivation, one of the motoneurons including a cell spheroid and a well grown and extended bundle of axon was brought outside the module 11 of the cultivation plate 10, as shown in FIG. 12(a). Its total length was 3.1 [mm]. Then, the proximal and distal ends of the axon bundle were picked up with tweezers and were pulled apart, so that the axon bundle was expanded to be 6.4 [mm]

long, as shown in FIG. 12(b). It was confirmed that the axon bundle had so much expandability as to be double.

As mentioned above, according to the present embodiment, an axon bundle integrated with a cell spheroid can be extracted or brought out from each of the modules 11 of the cultivation plate 10. And the axon bundle can be expanded mechanically, as confirmed by the above experiment. Therefore, by cultivating beforehand a desired sort of motoneuron integrated with an axon bundle, it is possible to accomplish a transplant of the axon bundles of motoneuron. While it has been difficult to examine or evaluate physical characteristics of axon bundles in a body system, it now becomes possible to pursue various experiments, such as expanding axon bundles or so, since axon bundles on a millimeter or more scale are available by the present embodiment.

Next will be described a result of experiment for calcium imaging of a bundle of grown axons accomplished by the present inventors using the cultivation plate 10.

Figure 13:
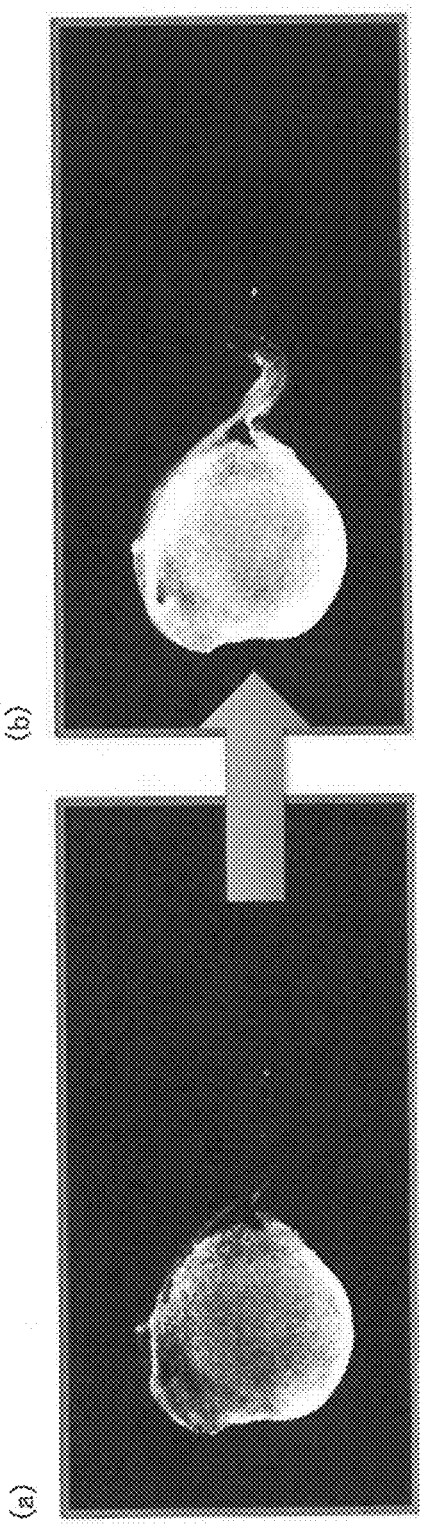
FIGS. 13(a)-13(b) are a set of photographs showing motoneurons used for calcium imaging.

FIG. 13 is a set of photographs showing motoneurons used for calcium imaging. In FIG. 13, (a) is a photograph of a spheroid with a bundle of axons outside the cultivation plate before adding calcium, (b) is a photograph of a spheroid with a bundle of axons outside the cultivation plate after adding calcium.

In the present experiment, motoneurons derived from human iPS cells (409B2 cell lines) were used. The cell spheroids of the motoneurons were inoculated in the first chambers 12a and cultivated. The motoneurons and the cell spheroids were gained in the same way as mentioned above and the cultivation was accomplished in the same way as mentioned above. After cultivation, one of the motoneurons with a well grown and extended bundle of axons was extracted or brought out from the module 11 of the cultivation plate 10. And the motoneuron including a cell spheroid and a bundle of axon received fluorescent treatment, as shown in FIG. 13(a). Then 1 [mol] of KCl was provided to the cell spheroid, so that fluorescence became intense, as shown in FIG. 13(b), as a result of electrophysiological activity induced by the stimulation of KCl. It was confirmed that the motoneuron including the cell spheroid and the bundle of axons became electrophysiologically active by providing KCl.

As mentioned above, according to the present embodiment, a motoneuron including a cell spheroid and a bundle of axons can be brought out from each of the modules 11 of the cultivation plate 10. And the motoneuron can be used for calcium imaging, as confirmed by the above experiment. Therefore, by cultivating beforehand a desired sort of motoneuron integrated with an axon bundle, it is possible to observe how a stimulus applied to the cell body is transferred through the axon, thus it is possible to apply to a development of technology of neural prosthesis, while it has been difficult, outside the body system, to evaluate electrophysiological activity of the bundle of axon.

Next will be described various examples of configuration of chambers 12a, 12b and channel(s) 13 in one module 11.

Figure 14:
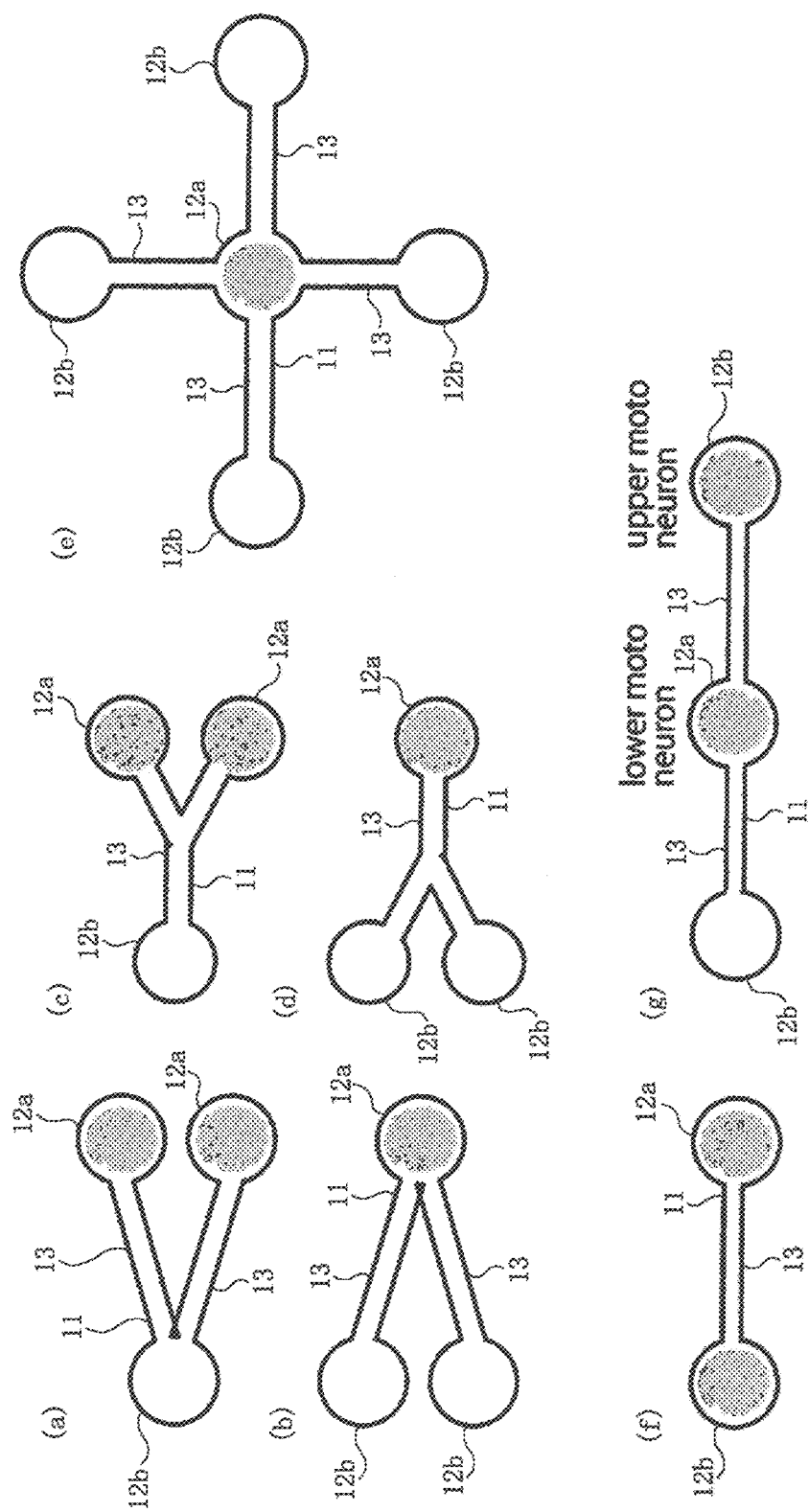
FIGS. 14(a)-14(g) are a set of schematic views of a variety of cultivation modules.

FIG. 14 is a set of schematic views of a variety of cultivation modules. In FIG. 14, (a)-(g) each shows a plan view of di rent type of configuration of chambers and channel(s).

In the present embodiment, the configuration of chambers 12a, 12b and channel(s) 13 in the module 11 is not necessary limited to such one that includes a pair of chambers 12a, 12b connected by one channel 13, as shown in FIGS. 3 and 4. According to one example shown in FIG. 14(a), the module 11 includes two of the first chambers 12a, in each of which a body spheroid is inoculated, one of the second chamber 12b, and two of the channels 13, each of which connects one of the first chambers 12a and the second chamber 12b. According to another example shown in FIG. 14(b), the module 11 includes one of the first chamber 12a, in which a cell body spheroid is inoculated, two of the second chambers 12b, and two of the channels 13, each of which connects the first chamber 12a and one of the second chambers 12b. According to one example shown in FIG. 14(c), the module 11 includes two of the first chambers 12a, in each of which a cell body spheroid is inoculated, one of the second chamber 12b, and one of the channel 13, which ramifies into two in its middle so as to connect two of the first chambers 12a and the second chamber 12b. According to another example shown in FIG. 14(d), the module 11 includes one of the first chamber 12a, in which a cell body spheroid is inoculated, two of the second chambers 12b, and one of the channel 13, which ramifies into two in its middle so as to connect the first chamber 12a and two of the second chambers 12b. According to another example shown in FIG. 14(e), the module 11 includes one of the first chamber 12a, in which a cell spheroid is inoculated, four of the second chambers 12b, and bar of the channels 13, each of which connects the first chamber 12a and one of the second chambers 12b.

As mentioned above, according to the present embodiment, once motoneurons are inoculated in the first chamber(s) 12a and are cultivated, axons grow in the channel(s) 13 and extend toward the second chamber(s) 12b, and, further, if skeletal muscles are inoculated in the second chambers) 12b, the distal ends of the axons and the skeletal muscles conjugate in the second chamber(s) 12b. Further, as shown in FIG. 14(f), it can be applied to a central nervous model by inoculating cell body spheroids in both the first chamber 12a and the second chamber 12b. Also, as shown in. FIG. 14(g), it can be applied to a system including lower and upper motoneurons and skeletal muscles by inoculating the cell body spheroids of lower motoneurons in the first chamber 12a, the cell body spheroids of upper motoneurons in one of the second chambers 12b and skeletal muscles in the other of the second chambers 12b. Therefore, when a variety of cultivation modules 11 is prepared, a variety of bans of conjugational relationship between neurons, axons and skeletal muscles can be achieved in vitro and can be used for a variety of experiments or researches of pharmaceutical products effective against neurological disorders.

Next will be described a way to separate axons from cell bodies in a module 11 of the cultivation plate 10 and to extract the axons and the cell bodies severally.

Figure 15:
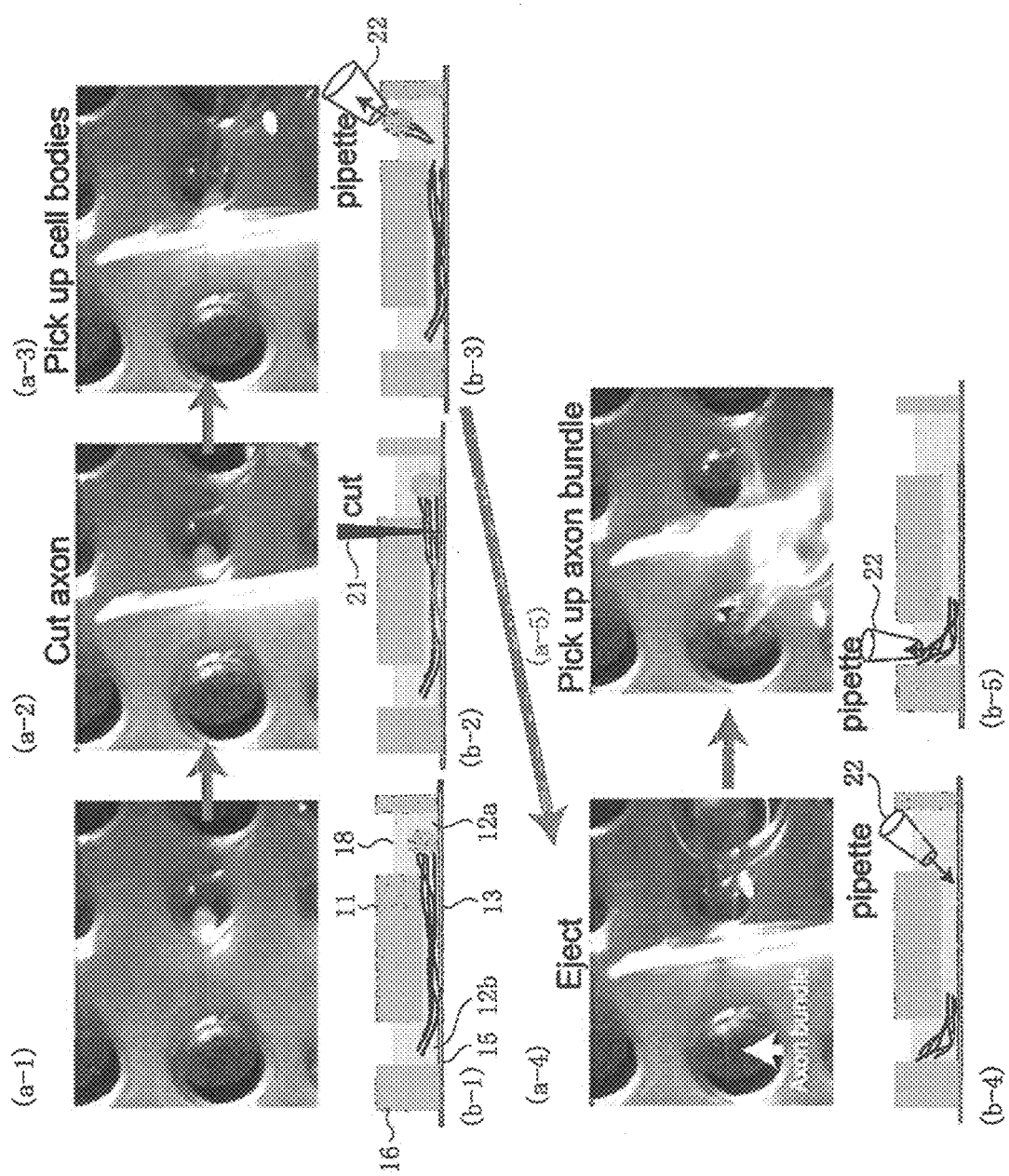
FIGS. 15(a-1) to 15(a-5) and FIGS. 15(b-1) to 15(b-5) are a set of views illustrating steps of separating axons from cell bodies.

FIG. 15 is set of views illustrating steps of separating axons from cell bodies. In FIG. 15, (a-1)-(a-5) each shows a photograph of an upper side of a module, (b-1)-(b-5) each shows a schematic cross sectional view of a module corresponding to (a-1)-(a-5) respectively.

According to the present embodiment, it is possible not only to extract the motoneurons including the mall bodies mid the axon bundle as a whole, as shown in FIG. 11-13, but also to separate the axon bundle from the cell bodies in a module 11 and to extract them severally. At first, the cell bodies of the motoneurons are inoculated in the first chamber 12a of the module 11 and cultivated, so that the axon bundle grows and extends from the first chamber 12a to the second chamber 12b through the channel 13, as shown in FIGS. 15(a-1) and (b-1). Then, the axon bundle is separated from the cell bodies by a cutter 21, as shown in FIGS. 15(a-2) and (b-2). In this case, at least the top board 16 is preferably made of soft material, such as PDMS, so that the cutter 21 can cut the axon bundle together with the top board 16 smoothly. Then, the cell bodies are brought out or picked up from the first chamber 12a by sucking with a pipette 22, as shown in FIGS. 15(a-3) and (b-3). Then, the remaining axon bundle is ejected from the channel 13 into the second chamber 12b with a flow of culture fluid 18 caused by blowing with the pipette 22, as shown in FIGS. 15(a-4) and (b-4). Finally, the axon bundle is brought out or picked up from the second chamber 12b by sucking with a pipette 22, as shown in FIGS. 15(a-5) and (b-5).

As mentioned above, according to the present embodiment, it is possible to separate the axon bundle from the cell bodies in the module 11 and to extract the axon bundle only. This may lead feasibly to analyses of protein or RNA existing only in the axon bundle. Such analyses are important processes for analyzing neurological disorders.

Next will be described usability of the device of the present embodiment for developing drugs effective against Amyotrophic Lateral Sclerosis (ALS).

Figure 16:
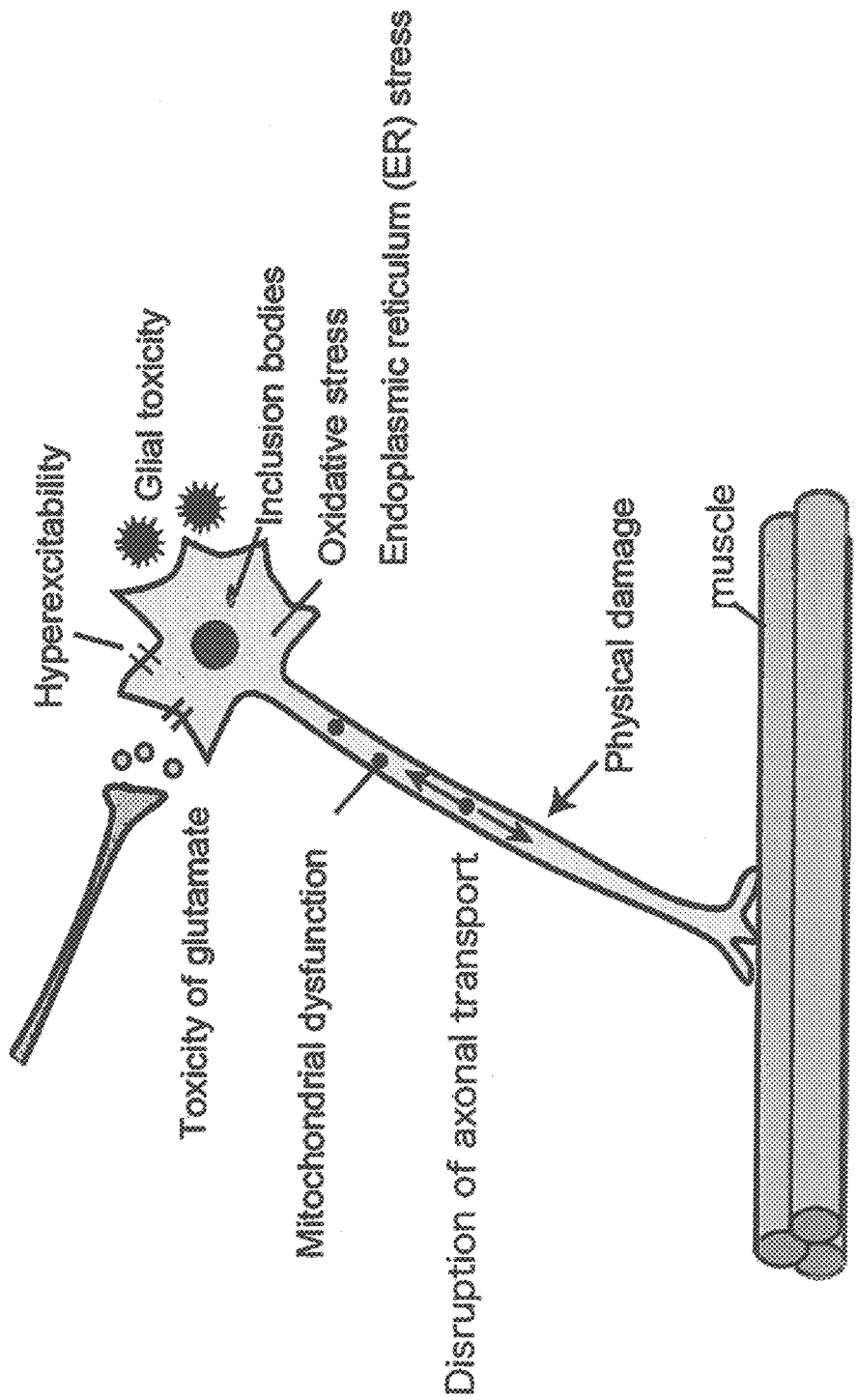
FIG. 16 is a schematic view showing causes of ALS.
Figure 17:
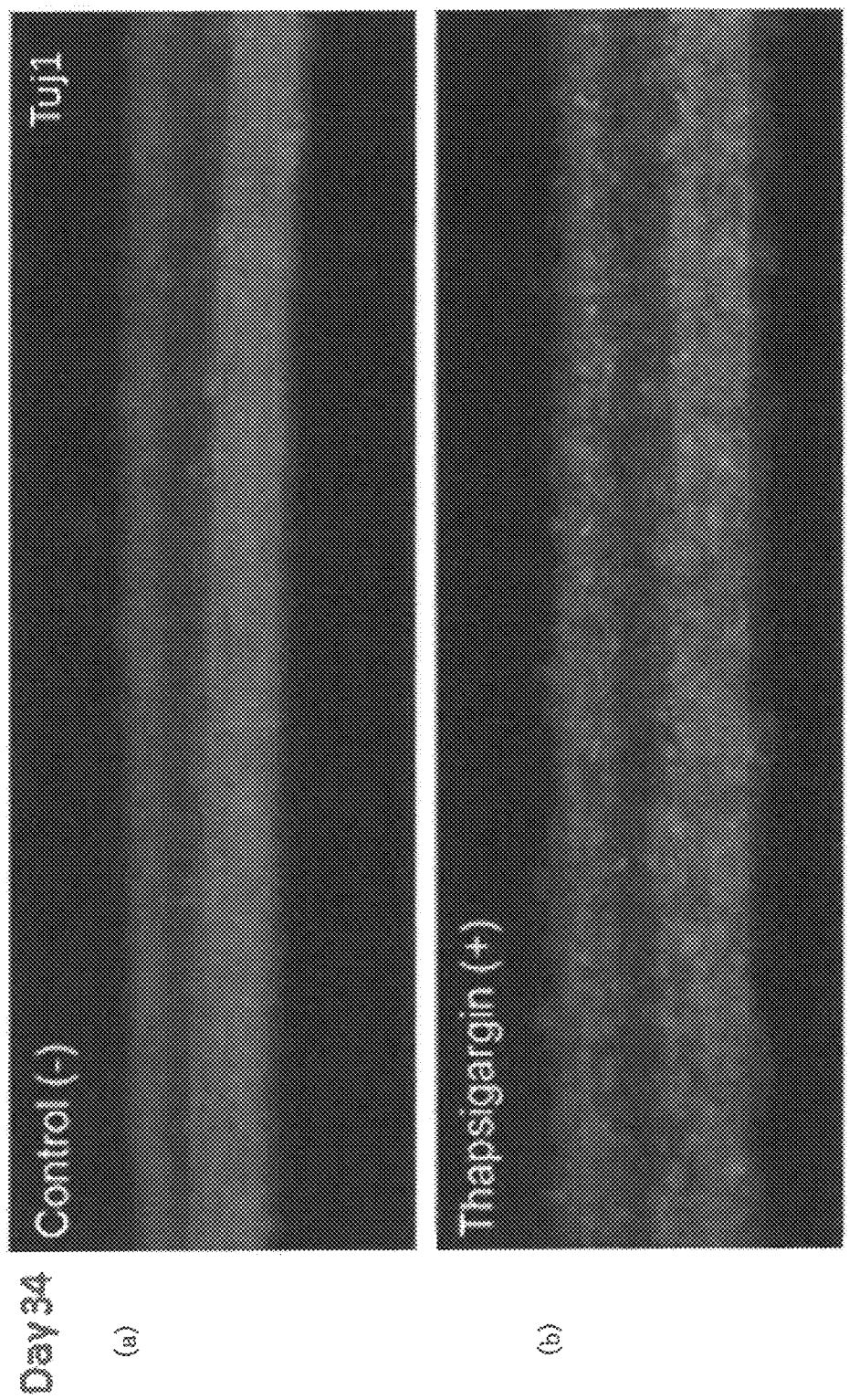
FIGS. 17(a)-17(b) are a set of photographs showing a result of stress test.
Figure 17A:
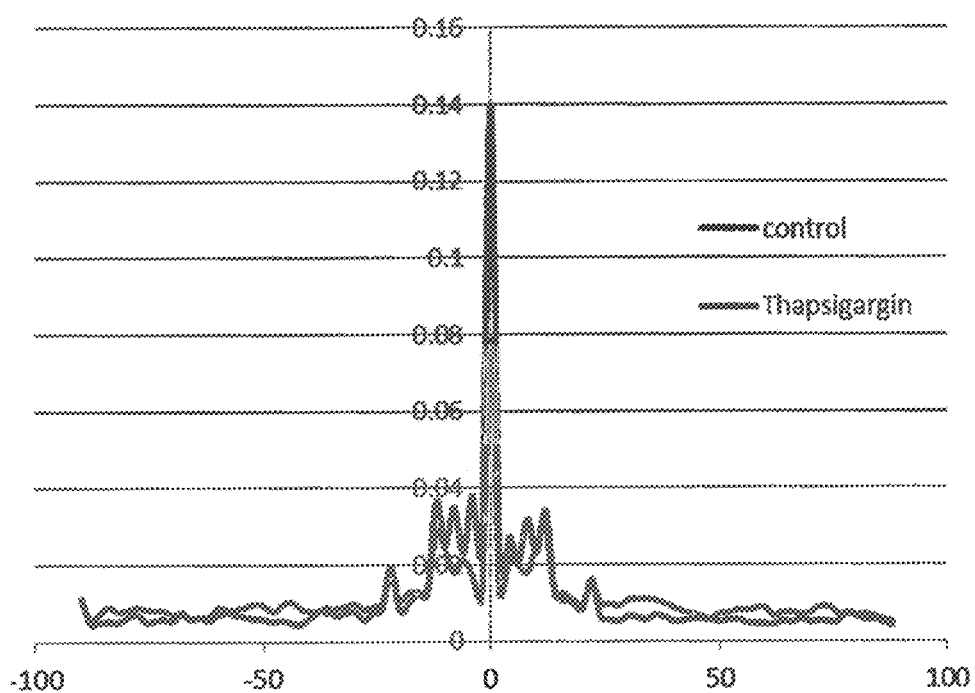
Figure 18:
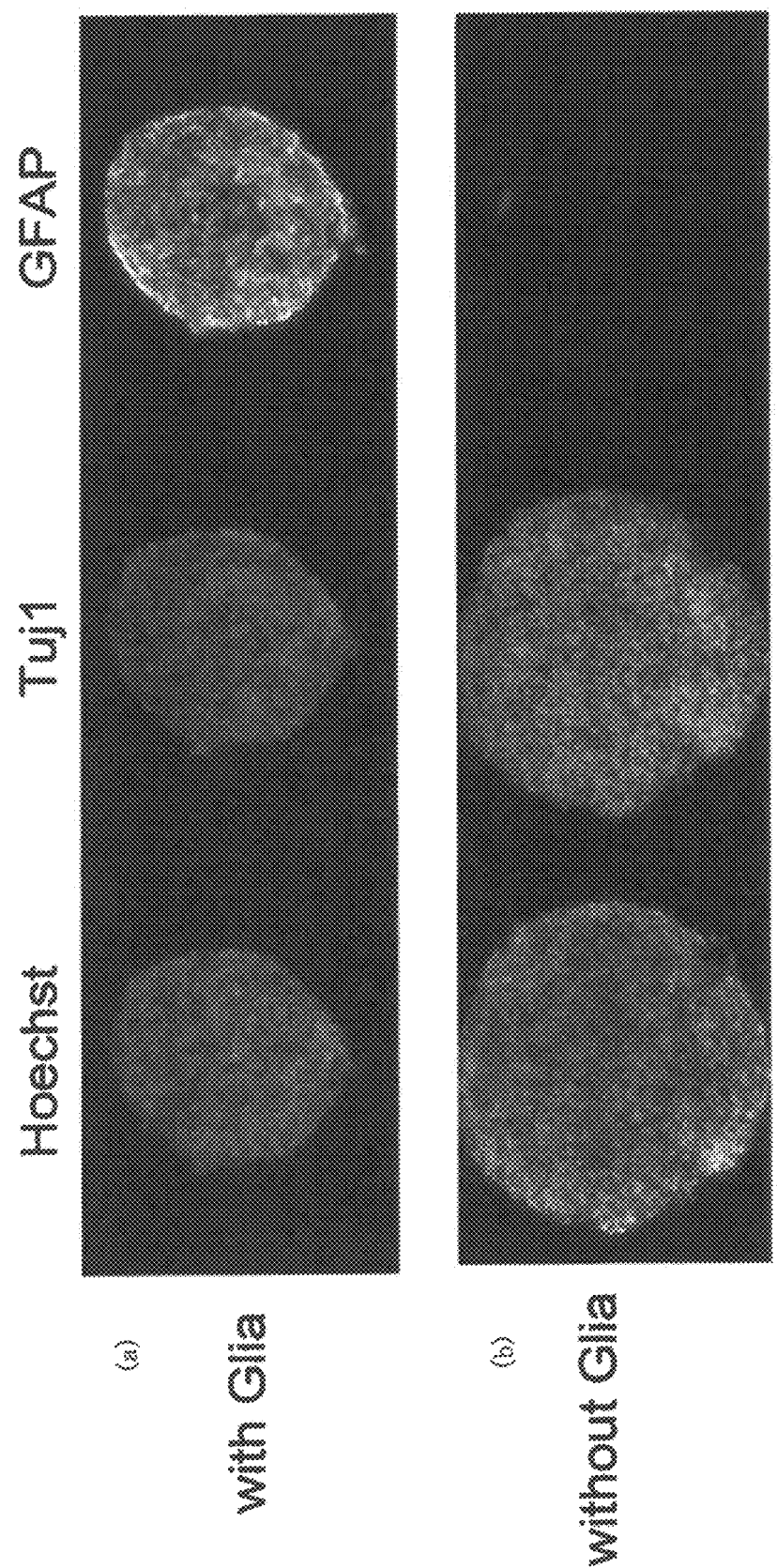
FIGS. 18(a)-18(b) are a set of photographs showing a result of co-cultivation with glia cells.
Figure 19:
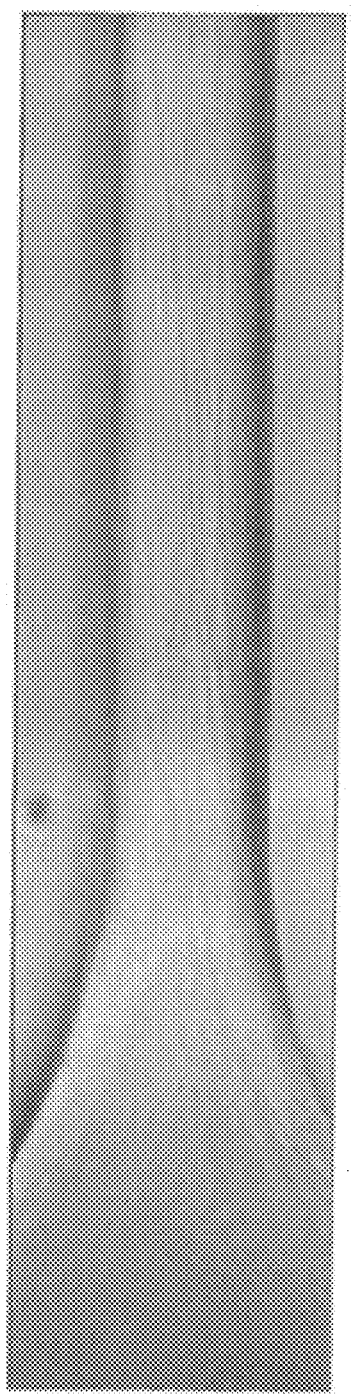
FIGS. 19(a)-19(b) are a set of photographs showing axon bundles extending from cell body spheroid with and without glia cells.
Figure 19:
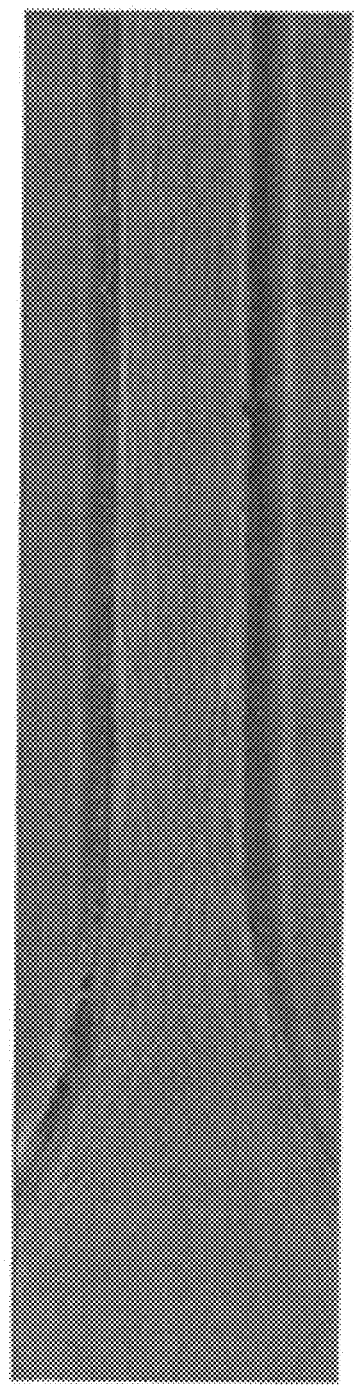

FIG. 16 is a schematic view showing causes of ALS. FIG. 17 is a set of photographs showing a result of stress test. FIG. 17A is a view of graph showing a result of evaluating orientation of an axon in stress test. FIG. 18 is a set of photographs showing a result of co-cultivation with glia cells. FIG. 19 is a set of photographs showing axon bundles extending from cell body spheroid with and without glia cells. In FIG. 17, (a) is a photograph of an axon bundle without stress, (b) is a photograph of an axon bundle with ER stress. In FIG. 18, is a photograph of a cell body spheroid with glia cells, (b) is a photograph of a cell body spheroid without glia cells. In FIG. 19, (a) is a photograph of an axon bundle with glia cells, (b) is a photograph of an axon bundle without glia cells.

The disease of ALS is considered to be caused by toxicity of glutamate, hyperexcitability, glial toxicity, mitochondria dysfunction, disruption of axonal transport, physical damage, oxidative stress, ER (endoplasmic reticulum) stress, inclusion bodies and so forth, as shown in FIG. 16. If any of these causes can be reproduced artificially, it would lead to discover drugs effective against ALS. For reproducing some of the causes, several experiments were accomplished by the present inventors using the cultivation plate 10 according to the present embodiment.

The first experiment was accomplished to confirm the effect of ER stress against motoneuron using thapsigargin. In the first experiment, motoneurons derived from human iPS cells (409B2 cell lines) were used. The cell body spheroids of the motoneurons were inoculated in the first chambers 12a and cultivated. The motoneurons and the cell body spheroids were gained in the same way as mentioned above and the cultivation was accomplished in the same way as mentioned above. After cultivation, one of the motoneurons with a well grown and extended axon bundle was treated with culture fluid including 1.5 [mol] of thapsigargin for 5 hours. Then, 6 days later, the form of the axon bundle was evaluated, as shown in FIG. 17(b), in comparison with another axon bundle of the motoneurons not treated with any thapsigargin, as shown in FIG. 17(a). Also, an evaluation of orientation of axon as shown in FIG. 17A was accomplished. It can be said that when suffering stress, the orientation of the axon becomes low or the axon degenerates. It was confirmed that the motoneurons subjected to ER stress became deformed.

As glia toxicity against ALS due to mutation of particular gene was under discussion, the second experiment was accomplished to confirm that the motoneurons can be co-cultivated with glia cells using the cultivation plate 10 according to the present embodiment. In the second experiment, motoneurons derived from human iPS cells (409B2 cell lines) were used. The cell body spheroids of the motoneurons were gained through cultivation in the first chambers 12a and cultivated, after glia cells were mixed with the motoneurons. Then the motoneurons were stained with such markers as Hoechst, Tuj1 and GFAP (Glia Fibrillary Acidic Protein). FIG. 18(a) shows the cell body spheroids of the motoneurons mixed with glia cells and FIG. 18(b) shows the cell body spheroids of the motoneurons not mixed with them. As GFAP is a marker to distinguish glia cells, it was confirmed that glia cells were uniformly distributed in the cell body spheroid. Further, after 10 days of cultivation, as shown in FIGS. 19(a) and 19(b), an axon bundle with non-existent glia cells grew and extended in the channel 13 from the cell spheroid even in the case of the motoneurons mixed with glia cells as shown in FIG. 18(a), as well as the case of motoneurons not mixed with them, as shown in FIG. 18(b). Thus, it was confirmed that a co-cultivation system with glia cells in the spheroid but not the axon bundle was available and it would be expected that the co-cultivation system with glia cells could be applied to reproduction of neurodegeneration by glial toxicity and to drug screening for development of drugs effective against ALS.

Next will be described a result of observation of axon bundles grown using the cultivation plate 10 according to the present embodiment on comparison with cell bodies.

Figure 20:
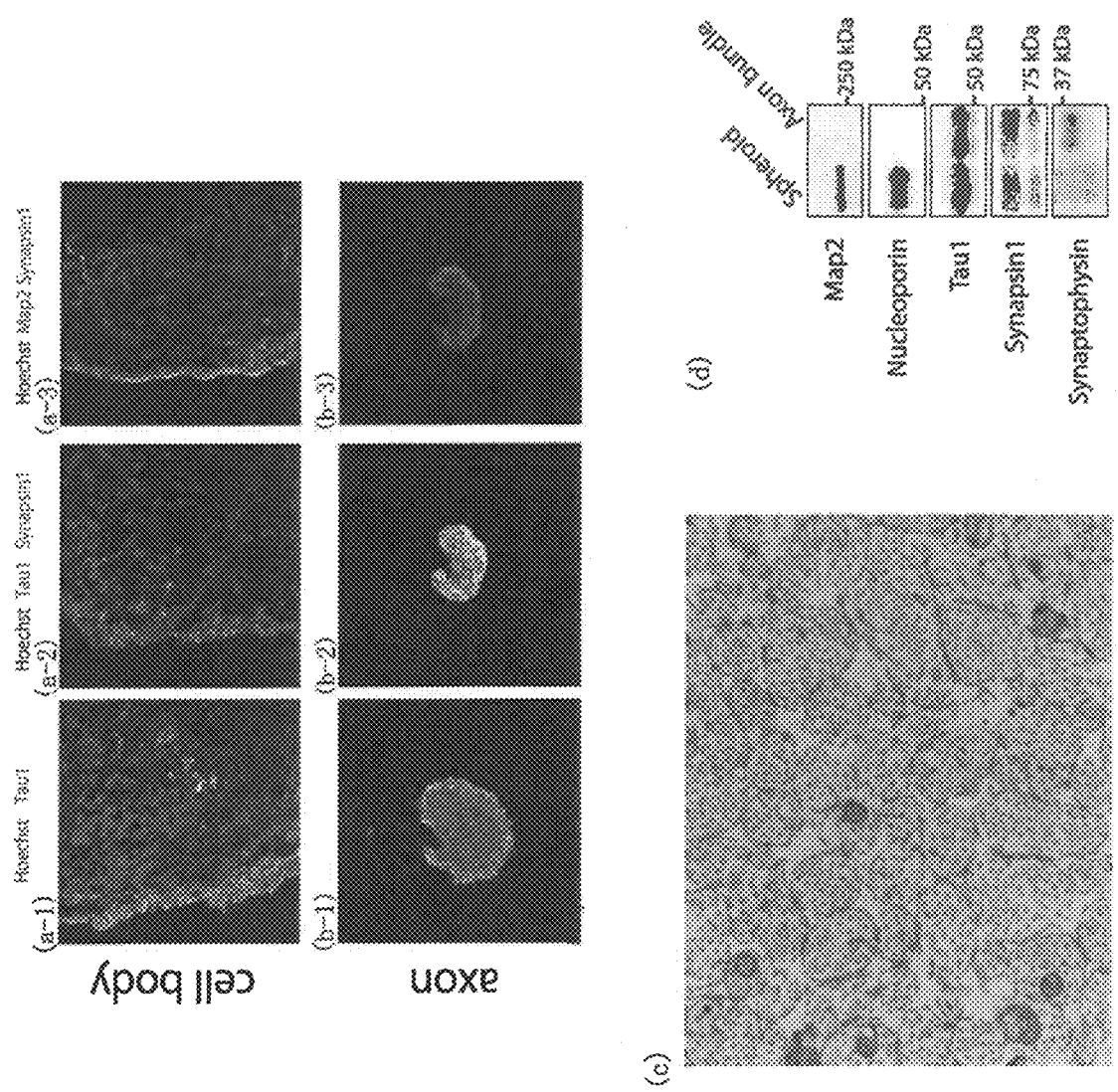
FIGS. 20(a-1) to 20(a-3), 20(b-1) to 20(b-3), 20(c) and 20(d) are a set of views showing a result of observation of bundles of axon grown in channels of the cultivation plate.
Figure 20A:
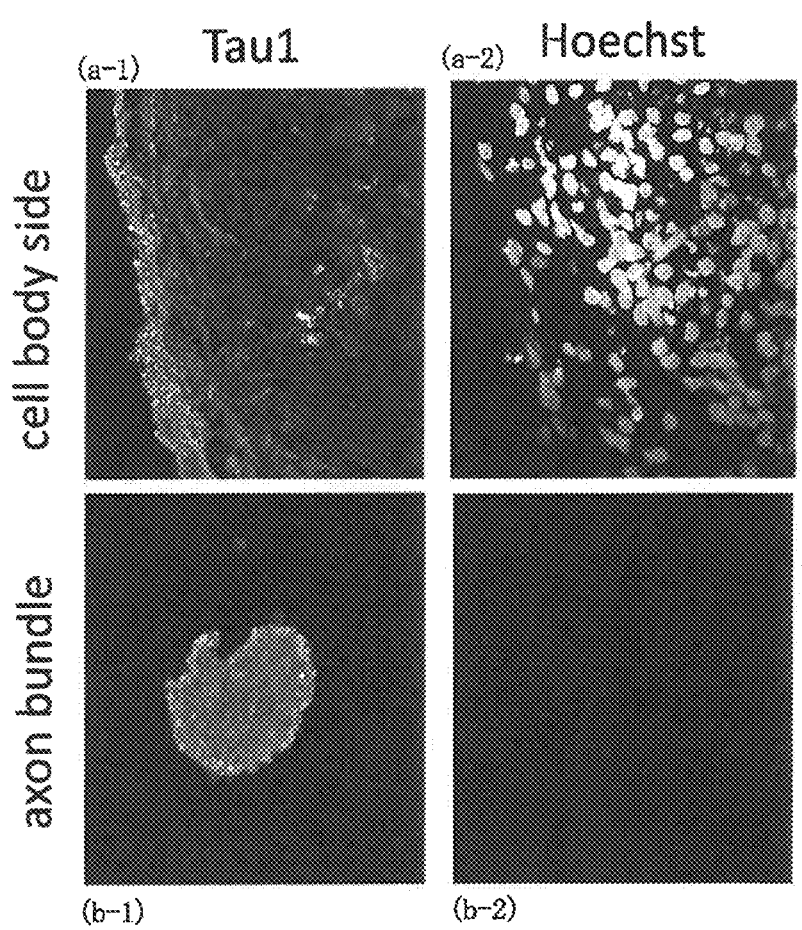
FIGS. 20A(a-1), 20A(a-2), 20A(b-1), and 20A(b-2) are a set of photographs showing sections of neurons including bundles of axon grown in channels of the cultivation plate.
Figure 20B:
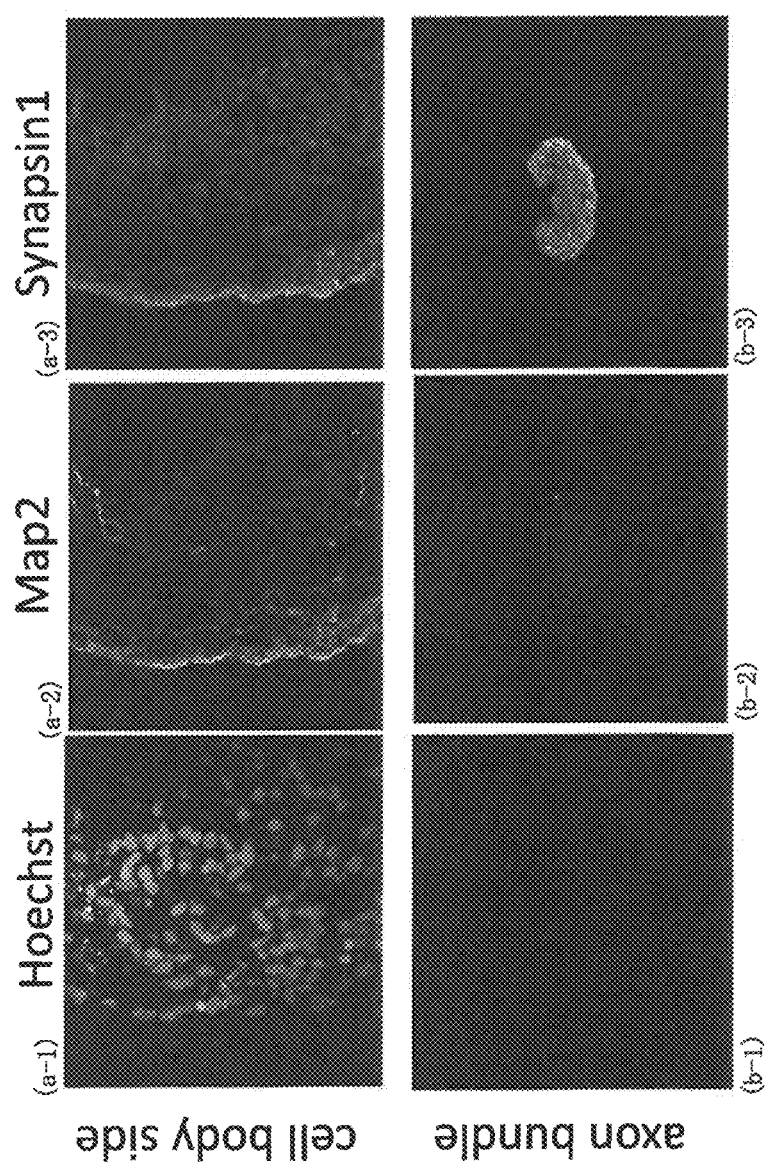
FIGS. 20B(a-1) to 20B(a-3) and 20B(b-1) to 20B(b-3) are another set of photographs showing sections of neurons including bundles of axon grown in channels of the cultivation plate.

FIG. 20 is a set of views showing a result of observation of bundles of axon grown in channels of the cultivation plate. FIG. 20A is a set of photographs showing sections of neurons including bundles of axon grown in channels of the cultivation plate. FIG. 20B is another set of photographs showing sections of neurons including bundles of axon grown in channels of the cultivation plate. In FIG. 20, (a-1)-(a-3) each shows a sectional photograph of a cell body stained by various makers, (b-1)-(b-3) each shows a sectional photograph of an axon bundle corresponding to (a-1)-(a-3) respectively (c) shows a transmission electron micrograph of a section of an axon bundle, (d) shows a set of views indicating results of protein analysis of cell bodies and axon bundles. In FIG. 20A, (a-1) and (a-2) each shows a sectional photograph of a cell body stained by various makers, (b-1) and (b-2) each shows a sectional photograph of an axon bundle corresponding to (a-1) and (a-2) respectively. In FIG. 20B, (a-1)-(a-3) each shows a sectional photograph of a cell body stained by various makers, (b-1)-(b-3) each shows a sectional photograph of an axon bundle corresponding to (a-1)-(a-3) respectively.

Here, motoneurons derived from human iPS cells (409B2 cell lines) were used. The cell body spheroids of the motoneurons were inoculated in the first chambers 12a and cultivated. The motoneurons and the cell body spheroids were gained in the same way as mentioned above and the cultivation was accomplished in the same way as mentioned above. After cultivation, one of the motoneurons with a well grown and extended bundle of axons was extracted or brought out from the module 11 of the cultivation plate 10. And a cell body spheroid and a bundle of axon were stained by such makers as Hoechst, Tau 1, Synapsin 1 and Map 2. FIG. 20(a-1)-(a-3) each shows a sectional photograph of a cell body stained by Hoechst and Tau 1, by Hoechst, Tau 1 and Synapsin 1, and by Hoechst, Map 2 and Synapsin 1 respectively, and FIG. 20(b-1)-(b-3) each shows a sectional photograph of an axon bundle corresponding to FIG. 20(a-1)-(a-3) respectively. FIGS. 20A(a-1) and (a-2) each shows a sectional photograph of a cell body stained by Tau 1, and by Hoechst and Tau 1 respectively, and FIGS.

20A(*a*-1) and (*b*-2) each shows a sectional photograph of an axon bundle corresponding to FIGS. 20A(*a*-1) and (*a*-2) respectively. FIG. 20B(*a*-1)-(*a*-3) each shows a sectional photograph of a cell body stained by Hoechst, by Map 2, and by Synapsin 1 respectively FIG. 20B(*b*-1)-(*b*-3) each shows a sectional photograph of an axon bundle corresponding to FIG. 20B(*a*-1)-(*a*-3) respectively. As axons are bundled, sections of axons are easily observed by immunostaining.

FIG. 20(*c*) shows a TEM image or a transmission electron micrograph of a section of an axon bundle. As axons are bundled, sections of plural axons are easily observed by a transmission electron microscopy. Thus, states of mitochondria, synapse and myotube in axon can be observed, and such an observation can be applied to evaluation of drug effects.

Furthermore, FIG. 20(*d*) shows a set of views indicating results of protein analysis, by known Western blotting or Western blot analysis, of cell bodies spheroid and axon bundles stained by such markers as Map 2, Nucleoporin, Tau 1, Synapsin 1 and Synaptophysin. [kDa] indicates a unit of kilodalton. As axons are bundled, an axon only sample can be recovered effectively and analysis of specific protein of axon can be available. In FIG. 20(*d*), as comparing the sample of axon bundle with one of cell body spheroid, it is found that, in the former, Map 2 and Nucleoporin, which are markers of cell body, are negative. Therefore, it is proved that the sample of axon bundle includes no cell body or is of high purity of axon. This is also proved by a fact that, in such immunostaining as shown by FIG. 20(*b*-1)-(*b*-3), FIGS. 20A(*b*-1) and (*b*-2), and FIG. 20B(*b*-1)-(*b*-3), both of Map 2, a cell body marker, and Hoechst, nuclei stain, are negative in samples of axon bundles. Synapsin 1 is observed both in axon bundles and in call bodies, since it exists in the whole neuron.

Next will be described a result of scanning electron microscopy observation of axon bundles grown using the cultivation plate 10 according to the present embodiment.

Figure 21:
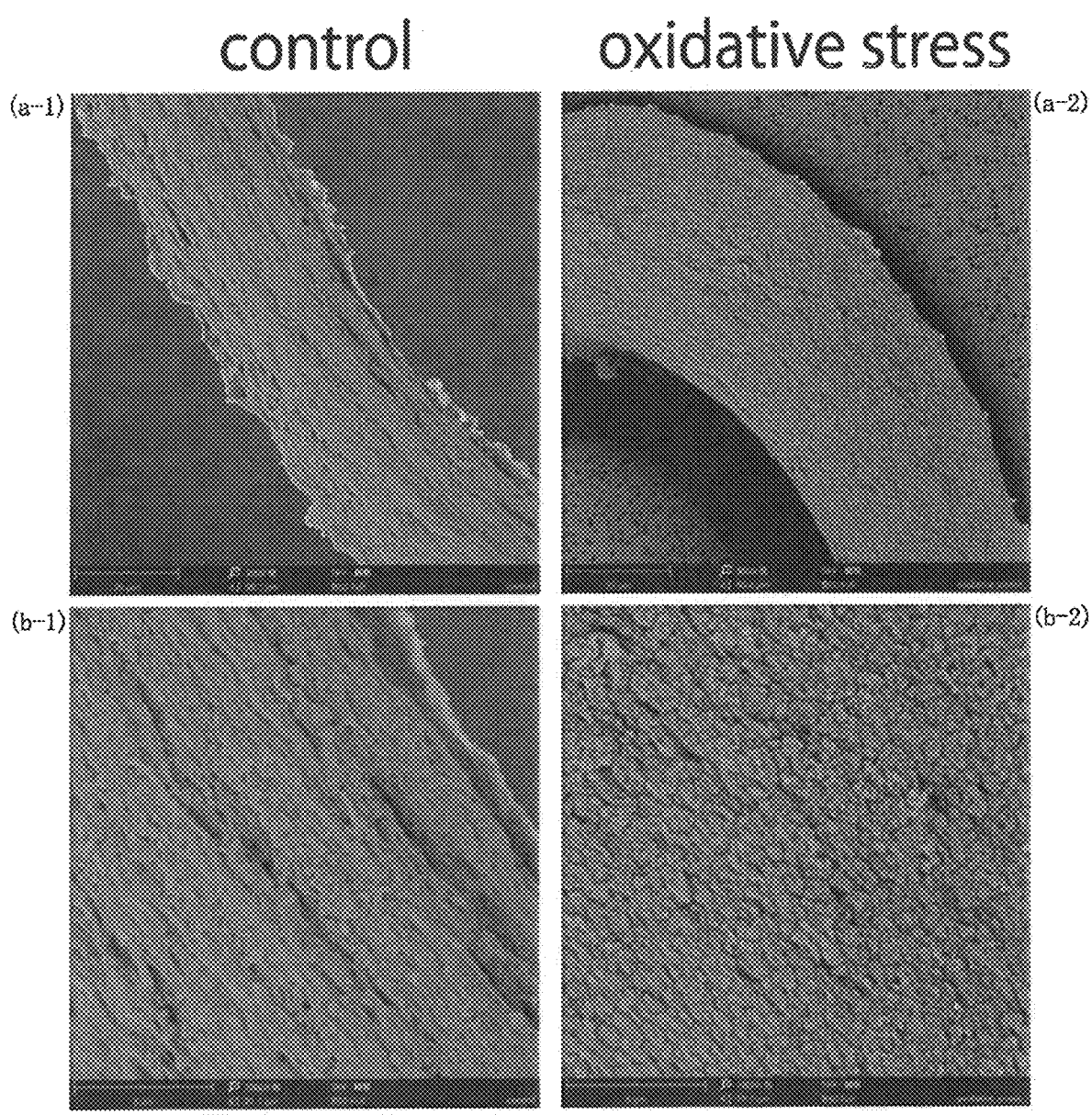
FIGS. 21(a-1), 21(a-2), 21(b-1), and 21(b-2) a set of photographs showing a result of scanning electron microscopy of surface of axon bundles grown in channels of the cultivation plate.

FIG. 21 is a set of photographs showing a result of scanning electron microscopy of surface of axon bodies grown in channels of the cultivation plate. In FIG. 21, (a-1) and (a-2) each shows a high and a low magnification photograph respectively in case of stress free, and (b-1) and (b-2) each shows a photograph in case of under stress corresponding to (a-1) and (a-2) respectively.

The axon bundle is the same as one used for observation shown by FIG. 20. As axons am bundled, the surface of axon bundle are easily observed by scanning electron microscopy. Also, as axons are bundled and extend in the same direction, the change under stress (oxidative stress in cases shown by FIGS. 21 (*b*-1) and (b-2)) are clear.

Next will be described under stress morphological change axon bundles grown using the cultivation plate 10 according to the present embodiment.

Figure 22:
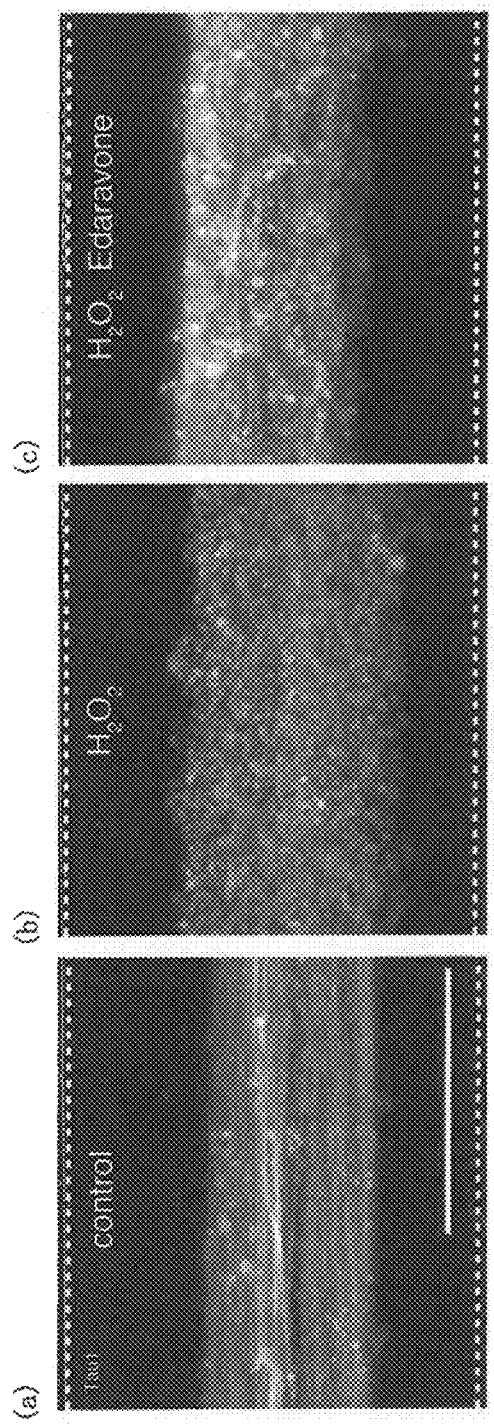
FIGS. 22(a)-22(c) are a set of photographs showing bundles of axon under stress in channels of the cultivation plate.
Figure 23:
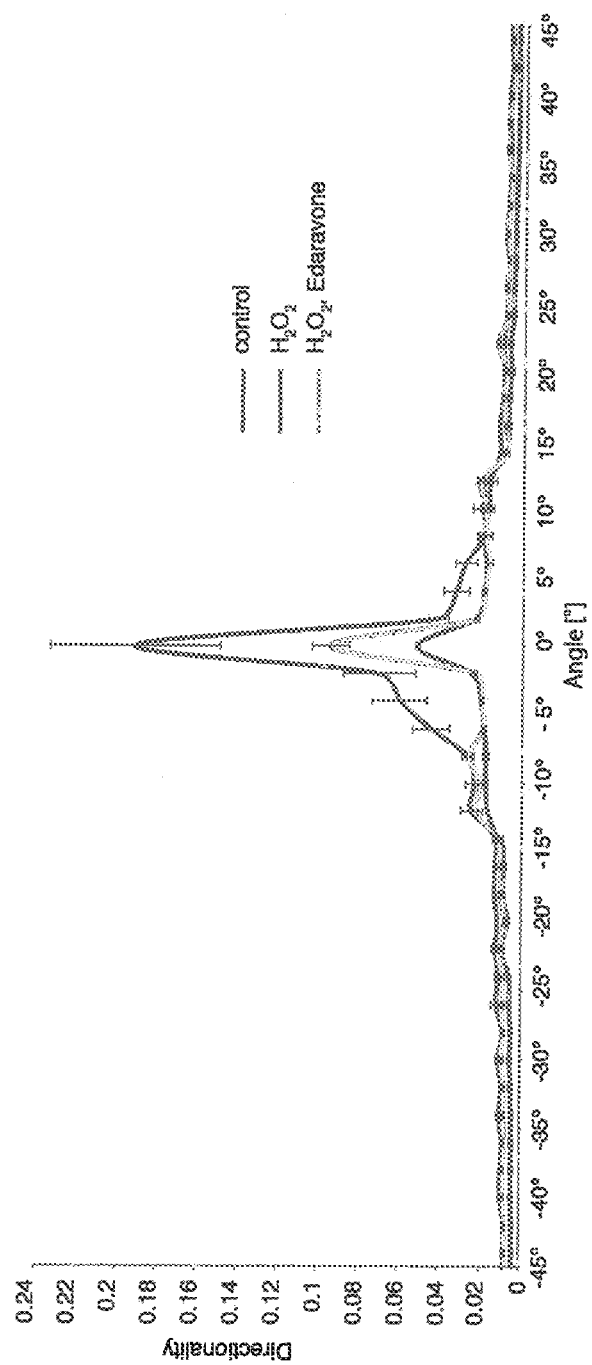
FIG. 23 is a view of graph showing an experimental result of morphological change of bundles of axon under stress in channels of the cultivation plate.

FIG. 22 is a set of photographs showing bundles of axon under stress in channels of the cultivation plate. FIG. 23 is a view of graph showing an experimental result of morphological change of bundles of axon under stress in channels of the cultivation plate. In FIG. 22, (a) shows a photograph in case of stress free, (b) shows a photograph in case of under oxidative stress, (c) shows a photograph in case of under oxidative stress and antioxidant.

Here, cell body spheroids were produced by inoculating motoneurons derived from human iPS cells (409B2 cell lines) in the nonadherent cultivation plate 10. Then, after 10 days of cultivation, the cell body spheroids were inoculated in the first chamber 12a of the module 11 of the cultivation plate 10. Then, after 30 days of cultivation, the treatments of the following (1)-(3) conditions were accomplished.

(1) control PBS (Phosphate Buffered Saline) washing>>>culture medium
(2) $H_2O_2$ 3 hour treatment>>>PBS washing>>>culture medium
(3) $H_2O_2$ 3 hour treatment>>>PBS washing>>>culture medium containing Edaravone Two days after the treatment, evaluation was done after immunostaining by marker Tau 1. The evaluation item was Directionality, which was the orientation of axon. Specifically, the orientations of objects in FIG. 22 were measured In this case, 0 degree indicated the direction of fluid conduit (channel 13). Since the axons were bundled and extended in the same direction, their morphological changes in the channel 13 could be compared between in case of under oxidative stress, as shown in FIG. 22(*b*), and in case of under oxidative stress accompanied by application of antioxidant (Edaravone), which was used as neurological disease drug, as shown in FIG. 22(*c*). The result of evaluation experiment, as shown in FIG. 23, indicated that, under oxidative stress, the axons extending in the axon direction degenerated, so that Directionality in the direction of fluid conduit (0 degree) reduced and the object deformed into complicated forms. As looking into Directionality of object shown in FIG. 23, observed was differences of Directionality in such an order that the highest was Directionality of the axon bundle in case of negative control or with no load, the second was in case of application of drug and stress, and the third was in case of under oxidative stress only. Therefore, it was found that the stress imposed on neuron could be evaluated as morphological change of axon based on image processing.

Next will be described myelination of axon bundles grown using the cultivation plate 10 according to the present embodiment.

Figure 24:
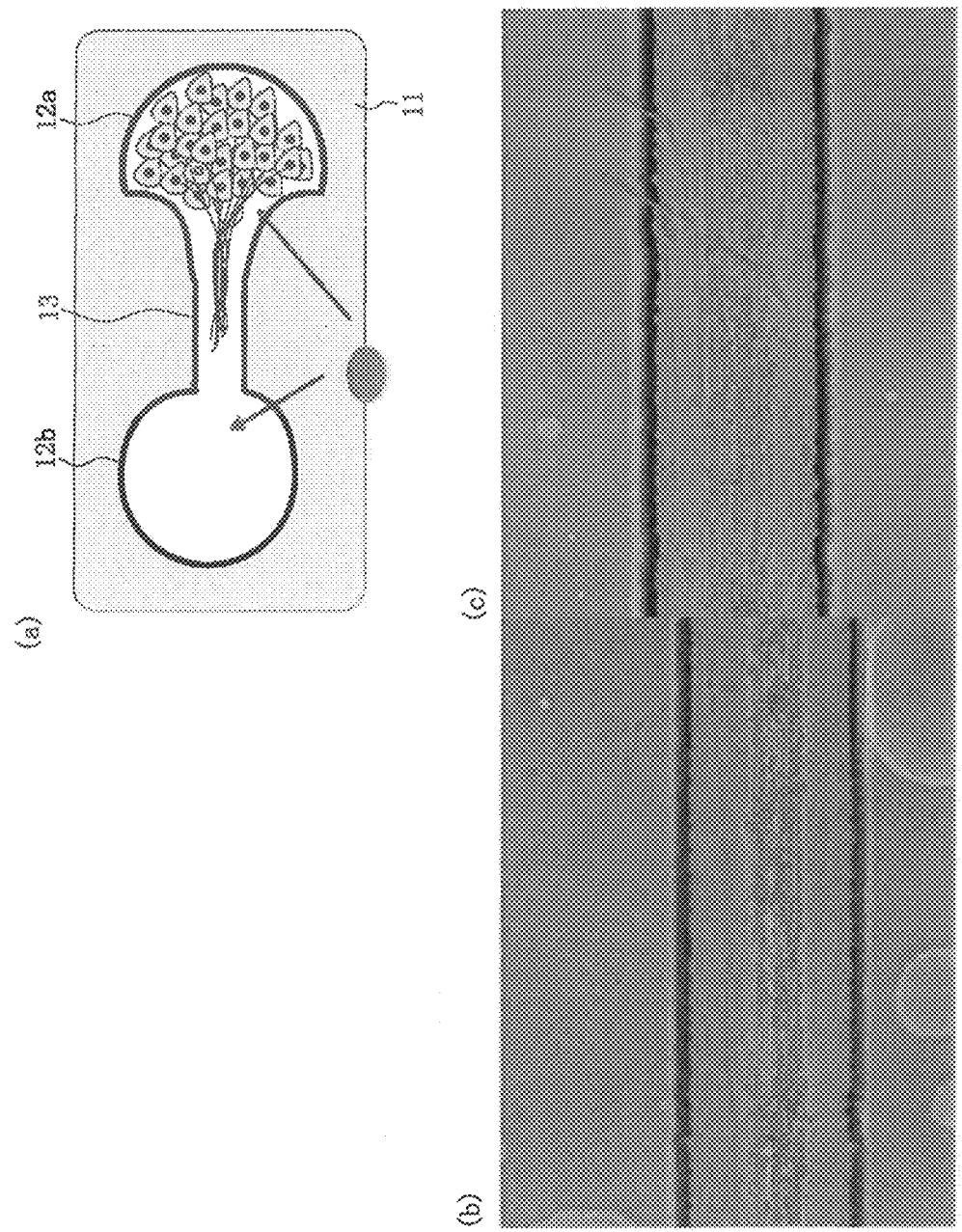
FIGS. 24(a)-24(c) are a set of views showing a myelination of axon in modules of the cultivation plate.

FIG. 24 is a set of views showing a myelination of axon in modules of the cultivation plate. In FIG. 24, (a) shows a schematic view explaining the myelination of neuron in the module, (b) shows a photograph of axons without Schwann cell, (c) shows photograph of axons with Schwann cells.

According to conventional ways of in vitro reproduction of myelination in the body system, as cell bodies of neuron were mixed with Schwann cells and cell bodies of oligodendrocyte, evaluation was complicated (identification of each cell body was difficult). Whereas, using the cultivation plate 10 according to the present embodiment, as shown in FIG. 24(*a*), it was easily observed how the axons and myelinated cells behaved since no cell body of neuron existed in the channel 13 of the module 11 or the opposite second chamber 12*b*. Specifically, IMS 32 cell lines were inoculated in the first chamber 12*a* and cultivated, then, after the axons were bundled, Schwann cells, cells for myelination, were inoculated. In comparison with the example without any Schwann cell as shown in FIG. 24(*b*), myelination could be easily observed in the example with Schwann cells as shown in FIG. 24(*c*).

Next will be described applicability of the device of the present embodiment.

Figure 25:
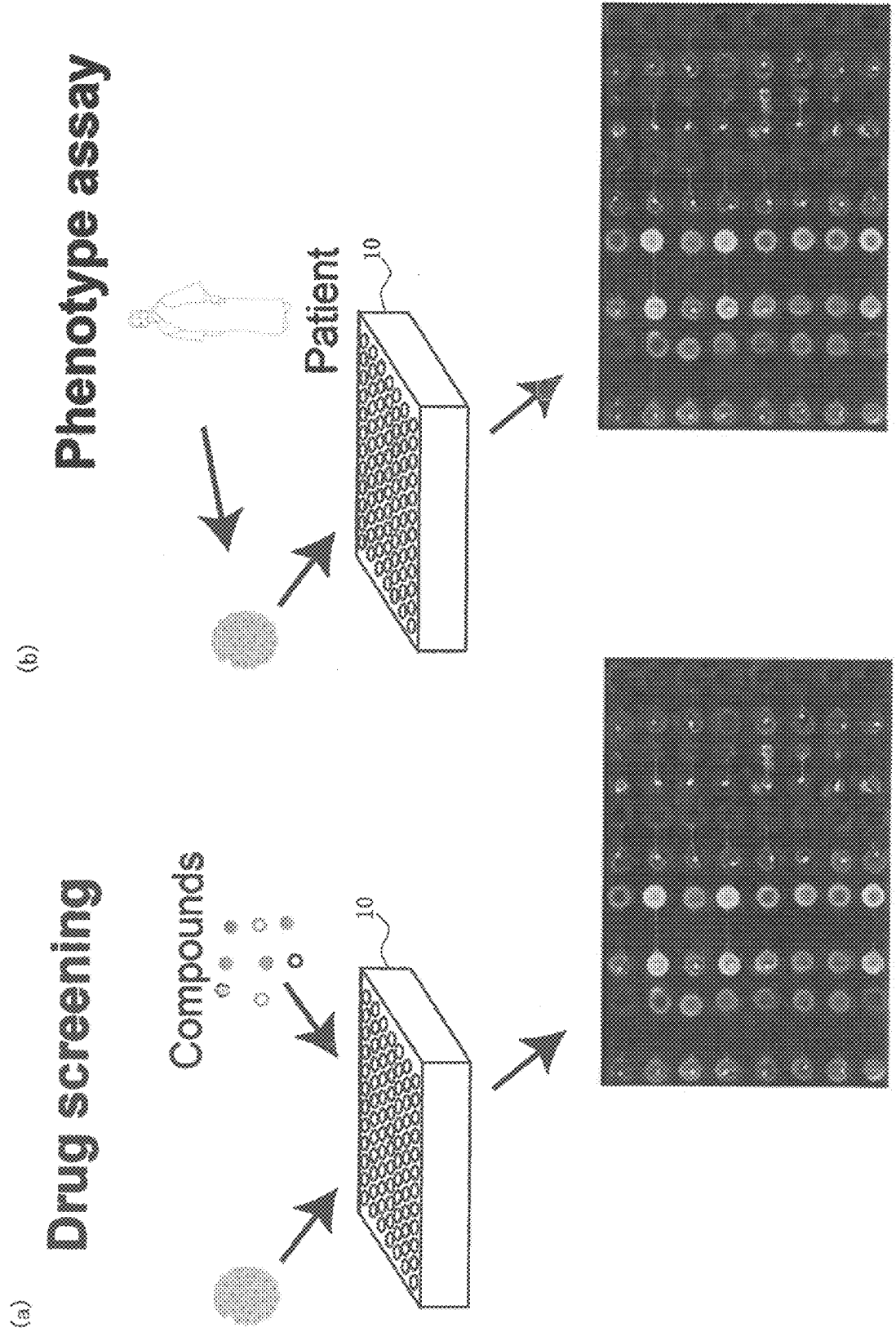
FIGS. 25(a)-25(b) are a set of schematic views showing applicable fields of the device.
Figure 26:
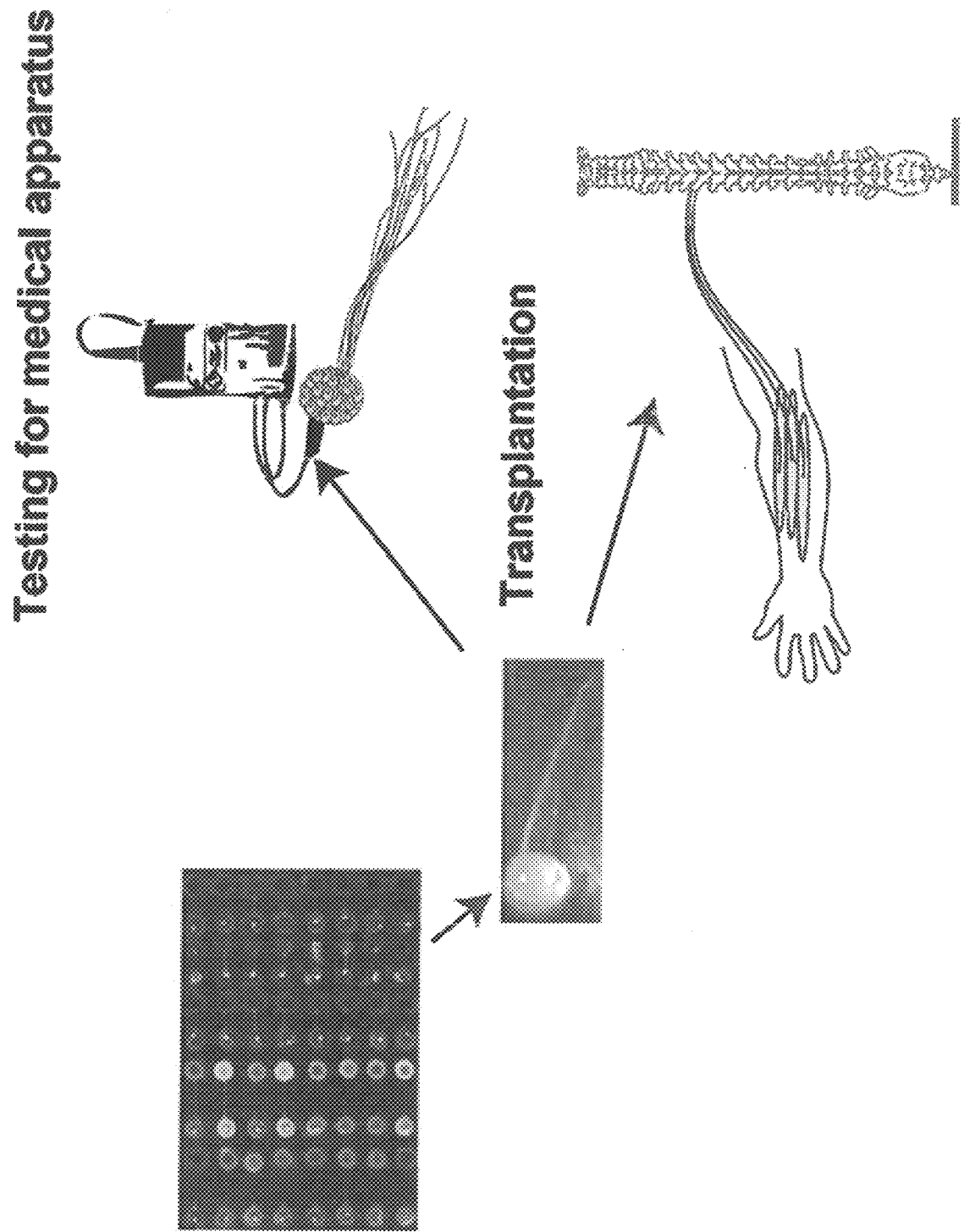
FIG. 26 is a set of schematic views showing another applicable field of the device.

FIG. 25 is a set of schematic views showing applicable fields of the device. FIG. 26 is a set of schematic views showing another applicable field of the device. In. FIG. 25, (a) shows an application to drug screening, (b) shows an application to phenotype assay.

With using the cultivation plate 10 according to the present embodiment, it would be available to accomplish screening co-cultivation systems of neural tissues or neurons with thick axon bundles and other tissues, as shown in FIG.

25 (a). Also, it would be possible to research phenotypes comprehensively by using tissues derived from patients, as shown in FIG. 25 (b). And the cultivation plate 10 is applicable to development of diagnostic drags by phenotype analysis. As shown in FIG. 26, neuro tissues with thick axon bundles, which are cultivated using the cultivation plate 10 according to the present embodiment, are usable for development or test of medical apparatuses, such as pacing systems. Also, they would be applicable to transplantation.

The disclosure in this Description describes characteristics regarding to the preferable and exemplary embodiments. Various other embodiments, modification and variations in the scope and the gist of the Claim(s) attached hereto would be reached by a person skilled in the art by referring to the disclosure in this Description.

INDUSTRIAL APPLICABILITY

The present disclosure is applicable to a device and a method suitable for cultivating neuron.

REFERENCE SIGNS LIST 10 cultivation plate
11 module
12a first chamber
12b second chamber
13 channel
15
16 top beard
17 seal member
18 culture fluid
21 cutter
22 pipette

The invention claimed is:

1. An aggregated neuron body consisting of a plurality of neurons with cell bodies derived from human iPS cells and axons extended from the cell bodies, the aggregated neuron body comprising:
 a spheroid and a bundle of axons of 1 mm or more in length extended from the spheroid in one direction, wherein the spheroid is an aggregation of a plurality of the cell bodies, and
 wherein the bundle of axons is a bundle of a plurality of the axons, glial cells being non-existent in the bundle of axons to a degree that a marker indicating existence of the glial cells is negative, wherein the marker is Glia Fibrillary Acidic Protein (GFAP).

2. The aggregated neuron body according to claim 1, wherein the bundle of axons is 4.5 mm or more in the length.

3. The aggregated neuron body according to claim 2, wherein the spheroid includes a glia cell.

4. The aggregated neuron body according to claim 2, wherein the aggregated neuron body is isolated.

5. The aggregated neuron body according to claim 2, wherein the aggregated neuron body is motoneuron.

6. The aggregated neuron body according to claim 5, wherein the bundles of axons conjugate at the axon terminal with skeletal muscle cells.

7. The aggregated neuron body according to claim 1, wherein the spheroid includes a glia cell.

8. The aggregated neuron body according to claim 7, wherein the aggregated neuron body is isolated.

9. The aggregated neuron body according to claim 7, wherein the aggregated neuron body is motoneuron.

10. The aggregated neuron body according to claim 9, wherein the bundles of axons conjugate at the axon terminal with skeletal muscle cells.

11. The aggregated neuron body according to claim 1, wherein the aggregated neuron body is isolated.

12. The aggregated neuron body according to claim 11, wherein the aggregated neuron body is motoneuron.

13. The aggregated neuron body according to claim 12, wherein the bundles of axons conjugate at the axon terminal with skeletal muscle cells.

14. The aggregated neuron body according to claim 1, wherein the aggregated neuron body is motoneuron.

15. The aggregated neuron body according to claim 14, wherein the bundles of axons conjugate at the axon terminal with skeletal muscle cells.

* * * * *